US006379714B1

(12) United States Patent
Khwaja et al.

(10) Patent No.: US 6,379,714 B1
(45) Date of Patent: *Apr. 30, 2002

(54) PHARMACEUTICAL GRADE BOTANICAL DRUGS

(75) Inventors: Tasneem A. Khwaja, Newport Beach; Elliot P. Friedman, Montecito, both of CA (US)

(73) Assignees: PharmaPrint, Inc., Santa Barbara; University of Southern California, Los Angeles, both of CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 524 days.

(21) Appl. No.: 08/632,273

(22) Filed: Apr. 15, 1996

Related U.S. Application Data

(63) Continuation-in-part of application No. 08/421,993, filed on Apr. 14, 1995, now abandoned.

(51) Int. Cl.$^7$ ............................................... A61K 35/78
(52) U.S. Cl. ....................... 424/725; 424/727; 424/730; 424/737; 424/754; 424/93.5; 514/783
(58) Field of Search .................... 424/195.1, 725, 424/727, 730, 737, 754, 93.5; 514/783

(56) References Cited

U.S. PATENT DOCUMENTS

| | | |
|---|---|---|
| 3,394,120 A | 7/1968 | Vester |
| 3,472,831 A | 10/1969 | Vester |
| 3,475,402 A | 10/1969 | Vester |
| 3,856,946 A | 12/1974 | Debat |
| 3,878,197 A | 4/1975 | Maret |
| 4,058,594 A | 11/1977 | Williams |
| 4,081,529 A | 3/1978 | Crippa |
| 4,313,930 A | 2/1982 | Wischniewski et al. |
| 4,368,195 A | 1/1983 | Madaus et al. |
| 4,525,344 A | 6/1985 | Tutsky |
| 4,590,071 A | 5/1986 | Scannon et al. |
| 4,614,733 A * | 9/1986 | Yoshikumi et al. ............ 514/54 |
| 4,749,573 A | 6/1988 | Bonne et al. |
| 4,758,433 A | 7/1988 | Johnson et al. |
| 4,784,849 A | 11/1988 | Tutsky |
| 4,820,689 A * | 4/1989 | Ikuzawa et al. ................ 514/8 |
| 4,857,327 A | 8/1989 | Virdalm |
| 4,857,512 A | 8/1989 | Wagner et al. |
| 4,861,581 A | 8/1989 | Epstein et al. |
| 4,871,763 A | 10/1989 | Madaus et al. |
| 4,894,443 A | 1/1990 | Greenfield et al. |
| 4,895,839 A | 1/1990 | Bombardelli |
| 4,966,577 A | 10/1990 | Crosson et al. |
| 4,997,649 A | 3/1991 | Papconstantin et al. |
| 5,019,368 A | 5/1991 | Epstein et al. |
| 5,093,475 A | 3/1992 | Carroll et al. |
| 5,096,708 A | 3/1992 | Gohla et al. |
| 5,183,904 A | 2/1993 | Carroll et al. |
| 5,202,313 A | 4/1993 | Bombardelli et al. |
| 5,211,948 A | 5/1993 | Cerise et al. |
| 5,244,885 A | 9/1993 | Carle et al. |
| 5,264,216 A | 11/1993 | Bombardelli et al. |
| 5,399,348 A | 3/1995 | Schwabe |
| 5,401,502 A | 3/1995 | Wunderlich et al. |
| 5,525,341 A | 6/1996 | Walker et al. |
| 5,531,992 A | 7/1996 | Yamazaki et al. |
| 5,543,146 A | 8/1996 | Perez |
| 5,547,673 A | 8/1996 | Bombardelli et al. |
| 5,565,199 A | 10/1996 | Page et al. |
| 5,646,178 A | 7/1997 | Walker et al. |
| 5,716,928 A | 2/1998 | Benet et al. |
| 5,770,217 A | 6/1998 | Kutilek et al. |
| 5,780,037 A | 7/1998 | Khwaja |
| 5,798,101 A | 8/1998 | Haveson |

FOREIGN PATENT DOCUMENTS

| | | |
|---|---|---|
| DE | 235 418 | 5/1986 |
| DE | 42 21 836 | 1/1994 |
| DE | 42 29 876 | 3/1994 |
| EP | 0 287 000 A1 | 10/1988 |
| EP | 0 552 439 A1 | 7/1993 |
| EP | 602 686 | 6/1994 |
| EP | 0 702 957 A1 | 3/1996 |
| WO | WO 96/20284 | 7/1996 |
| WO | WO 96/28178 | 9/1996 |
| WO | WO 96/37209 | 11/1996 |

OTHER PUBLICATIONS

Hobbs, Handbook for Herbal Healing, Botanica Press, 1990, pp. 30–32.*

Trypsteen et al, Analyst 114: 1021–1024, 1989.*

Chialva et al, J. Chromatogr. 279:333–340, 1983.*

Sharma, Biological Abstracts 82: 16049, 1986.*

Hatinguais et, al, Chemical Abstracts 99:10736c, 1983.*

Rossi, "Biological Testing", Chapter 31 of *Remington's Pharmaceutical Sciences*, Osol et al, editors, pp. 520–531, 1980.*

IX$^{th}$ International Conference on AIDS, Abstract #PO–B28–2167, p. 496, 1993.*

Battera–Arellano et al., 1990, "Antioxidant Activity of Brazilian Plant Extract", Seifen, Öle, Fette, Wachse 116(2):56–58.

Hatinguais et al., 1981, Trav. Soc. Pharm. Montpellier 41(4): 253–262 (and English translation).

(List continued on next page.)

*Primary Examiner*—Francisco Prats
(74) *Attorney, Agent, or Firm*—Lyon & Lyon LLP

(57) ABSTRACT

A method for making and identifying processed botanical materials as being of a pharmaceutical grade for use in clinical settings and patient treatment. The method utilizes fingerprints of the processed botanical material with respect to bioactivity and/or composition to establish whether the material meets previously established pharmaceutical grade requirements. The method is applicable to processed botanical materials, such as plant extracts, powders and the like which are used in medicinal applications.

31 Claims, 4 Drawing Sheets

OTHER PUBLICATIONS

Sharma, Nutr. Reports Int. 33(4):669–677, 1986.

Bauer, 1996, "Echinacea: Biological Effects and Active Principles", 212$^{th}$ ACS National Meeting, Orlando, FL. (Abstract No. 073).

Bauer, 1993, "Echinacea Species as Potential Immunostimulatory Drugs", Economic and Medicinal Plant Research, vol. 5 (Academic Press, New York) pp. 254–321.

Bauer, 1988, "Echinacea", Deutche Apotheker. Zeit. 128:174–180 (and translated summary).

Cristoni et al., 1997, "Chemical and Pharmacological Study on Hyprcritical $CO_2$ Extracts of Serona repens fruits", Fitoterapia 68:355–358.

De Swaef et al., 1996, "Supercritical Fluid Chromatography of Free Fatty Acids and Ethyl Esters in Ethanolic Extracts of Sabal serrulata", Phytochem. Anal. 7:223–227.

Dingerman, 1995, "Phytopharmaceuticals in Old Age", Pharm. Zeit. 140:9–14 16 (and translated abstract).

Dunaev et al., 1987, "Biological Activity of the Sum of Valepotriates Isolated from Val. Alliariifolia Adams", Farmakologiia Toksikologiia 50:33–37 (and translated abstract).

Ferreira et al., 1996, "Effect of Extracts of Valerina officnalis on [$^3$H]GABA", Rev. Port. Farm. 46:74–77.

Galletti et al., 1996, "Essential Oil Composition of Leaves and Berries of Vitex agnus–castus L. from Calabria, Southern Italy", Rapid Comm. Mass Spectrometry 10:1345–1350.

Gizella et al.,1994, "Spectrophotometric and Chromatographic Investigation of Bilberry Antocyanins fro Qualification Purposes", Acta Pharm. Hungaria 64:117–122 (and translated abstract).

Han et al., 1991, "The Screening of Chinese Traditional Drugs by Biological Assay and the Isolation of Some Active Components", Int. J. Chinese Med. 16:1–17.

Illes et al., 1996, "Supercritical Extraction", Olaj. Szappan Kosmet 45:20–25 (and translated abstract).

Kilmer, 1996, "How LC/MS Can Help Solve Your Pharmaceutical Analysis Problems", Today's Chemist at Work, Feb. pp. 39–44.

Krawczyk and Petri, 1990, "Application of RP–HPLC and Spectrophotometry in Standardization of Bilberry Anthocyanin Extract", Arch Pharm. 325:147–149.

Kustrak et al., 1994, "Determination of the Flavonoid Content of Chaste Tree", Farm. Glas. 50:321–339 (and translated summary).

Mennini et al., 1993, "In Vitro Study on the Interaction of Extracts and Pure Compounds from valeriana officinalis Roots with GABA, Benzodiazepine and Barbiturate Receptors in Rat Brain", Fitoterapia 64:291–300.

Nissen, 1987, "Quality Control of Phytopharaca with HPLC,", GIT Fachz Lab 31:293–295 (and translated abstract).

Rocha, 194, "An Antigungal y–Pyrone and Xanthones with Monoamine Oxidase Inhibitory Activity from Hypericum Brasiliense", Phytochem. 36:1381–1385.

Seabra,1992, "Analysis of Commercially Available Hypericum Extracts", Rev. Port. Farm. 41:39–42 (and translated abstract).

Shimada, 1997, "Biologically Active Acylglycerides from the Berries of Saw Palmetto", J. Nat. Prod. 60:417–418.

Zhang and Wu, 1984, "Preparation and Quality Control of Water Soluble Silybin and its Preparations", Yaoxue Tongbao 19:7–8 (and translated abstract).

S. Krager AG, "Cancer of the Exocrine Pancreas," *Oncology*, vol. 12, pp. 1–70, 1986.

Gabius et al., "Cytokines as Mediators in Rationally Standardized Mistletoe Therapy," Abstracts of the Third International Conference of Anticancer Research, 16–20 Oct. 1990, Marathon, Greece, No. 385, pp. 1473–1474.

Rentea et al., "Biologic Properties of Iscador: A Viscum album Preparation," *Laboratory Investigation,* Vo. 44, No. 1, pp. 43–48, 1981.

Ribéreau–Gayon et al., "Effects of mistletoe (*Viscum album* L.) extracts on cultured tumor cells," *Experientia 42,* pp. 594–599 (1986).

Gabius et al., "The immunomodulatory β–Galactoside–Specific Lectin from Mistletoe: Partial Sequence Analysis, Cell and Tissue Binding, and Impact on Intracellular Biosignalling of Monocytic Leukemia Cells," *Anticancer Research* 12:669–676 (1992).

Kayser et al., "Analysis of tumour necrosis factor α–specific, lactose–specific and mistletoe lectin–specific binding sites in human lung carcinomas by labelled ligands," *Virchows Archiv A Pathol Anat* (1992) 421:345–349.

Gabius et al., "The galactoside–specific lectin from mistletoe as biological response modifier," *Int'l Journal of Oncology*, 1, 705–708, 1992.

Hajto, "Modulatory Potency of the β–Galactoside–specific Lectin from Mistletoe Extract (Iscador) on the Host Defense System in Vivo in Rabbits and Patients," *Cancer Research,* 49, 4803–4808, 1991.

Beuth et al., "Behavior of lymphocyte subsets and expression of activation markers in response to immunotherapy with galactoside–specific lectin from mistletoe in breast cancer patients," *Clin. Investig.* (1992) 70:658–661.

Bloksma, "Stimulation of Humoral and Cellular Immunity by Viscum Preparations," pp. 2–8.

Khwaja et al., "Experimental Basis for the Use of 'Iscador' in Cancer Treatment," *13th International Congress of Chemotherapy,* Vienna 28th August to 2nd Sep. 1983.

Khwaja et al., "Isolation of biologically active alkaloids from Korean mistletoe *Viscum albu, coloratum*," Experientia 36 (1980).

Khwaja et al., "Studies on Cytotoxic and Immunologic Effects of *Viscum Album* (Mistletoe)," AACR 22, 253, 1981.

Khwaja et al., "Isolation of Cytotoxic Proteins from *Viscum Album, coloratum*," AACR Abstract Form, 1985.

Khwaja et al., "Isolation of Cytotoxic Lectin from *Viscum Album, Coloratum*," Proceedings of AACR, vol. 28, Mar. 1987, p. 303.

Khwaja et al., "Characterization of Biologically Active Components of *Viscum Album* (Mistletoe)," Poster Abstract Form for publication in the *Journal of Cancer Research Oncology*, 1989.

Khwaja et al., "Characterization of cytotoxic lectins isolated from *Viscum album, coloratum*," AACR, vol. 30, p. 576, 1989.

Khwaja et al., "Characterization of biologically active components of Mistletoe," AACR, 1990.

Khwaja et al., "Biopharmacological Studies of Different Components of *Viscum album* (Mistletoe)," Abstracts of the Third International Conference of Anticancer Research, pp. 1374–1375, 1990.

Bazylak et al., 1996, "Systematic analysis of glucoiridiods from *Penstemon serrulatus* Menz. by high–performance liquid chromatography with pre–column solid–phase extraction", J. Chromatogr. A 725:177–187.

Habtemariam et al., 1993, "The muscle relaxant properties of *Portulaca oleracea* are associated with high concentrations of potassium ions", J. Ethnopharmacology 40:195–200.

Hayashi et al., 1992, "Scoparic Acid A, A β–Glucuronidase Inhibitor From *Scoparia Duclis*", J. Natural Products 55(No. 12): 1748–1755.

Heptinstall et al., 1992, "Parthenolide Content and Bioactivity of Feverfew (*Tanacetum parthenium* (L.) Schultz–Bip.) Estimation of Commercial and Authenticated Feverfew Products", J. Pharm. Pharmacol. 44:391–395.

Heptinstall, 1988, "Feverfew—an ancient remedy for modern times?", Journal of the Royal Society of Medicine 81:373–374.

Peraza–Sanchez et al., 1992, "Isolation of Picropolygamain From The Resin of *Bursera Simaruba*", J. of Natural Products 55(No. 12):1768–1771.

Apitz–Castro et al., 1983, "Effects of Garlic and of Three Pure Components Isolated from it on Human Platelet Aggregation, Arachidonate Metabolism, Release Reaction and Platelet Ultrastructure", Thrombosis Res. 32:155–169.

Carle and Gomaa, 1992, "Chamomile: A Pharmacological and Clinical Profile", Drugs of Today 28:559–565.

Davies et al., 1992, "Kava Pyrones and Resin: Studies on $GABA_A$, $GABA_B$ and Benzodiazepine Binding Sites in Rodent Brain", Pharmacol. & Toxicol. 71:120–126.

Drieu, 1986, "Preparation et Definition de l'extrait de Ginkgo biloba," La Presse Medicale 15:1455–1457.

Eyers and Fenton, 1984, "A Chemical and Commercial Background to Evening Primrose Oil", Chem. NZ 48(6):52–56.

Gawlik et al., 1992, "Antiproliferative Effect of Mistletoe–Extracts in Melanoma Cell Lines", Anticancer Research 12(6A):1882.

Kamanna and Chandrasekhara, 1984, "Hypocholesteremic Activity of Different Fractions of Garlic", Indian J. Med. Res. 79:580–583.

Liberti and Marderosian, 1978, "Evaluation of Commercial Ginseng Products", J. Pharmaceutical Sci. 67:1487–1489.

Mitscher et al., 1990, *Antimutagenesis and Anticarcinogenesis Mechanisms* Plenum Press, New York) pp. 153–165.

Obermeier et al., 1995, "Effects of Bioflavonoids on Hepatic P450 Activities", Xenobiotica 25:575–584.

Sagesakai–Mitane et al., 1990, "Platelet Aggregation Inhibitors in Hot Water Extract of Green Tea", Chem. Pharm. Bull. 38:790–793.

Sharma and Sunny, 1988, "Effects of Garlic Extracts and of Three Pure Components Isolated from it on Human Platelet Aggregation, Arachidonate Metabolism, Release Reaction and Platelet Ultrastructure—Comments", Thrombosis Res. 52:493–494.

Suga and Hirata, 1983, "The Efficacy of the Aloe Plants Chemical Constituents and Biological Activities", Cosmetics & Toiletries 98:105–108.

Tittel and Wagner, 1978, "Hochleistungsflussigchromatographisce Trennung und Quantitative Bestimmung von Valepotriaten aus Valeriana–Drogen und Zubereitungen", J. Chromatography 148:459–468.

Todorov et al., 1984, "Pharmacokinetics and Mechanism of Action of *Eleutherococcus Glycosides*", Khimiko–farmatsevticheskii Zhurnal 18:920–924.

Weinberg et al., 1993, "Identification and Quantification of Organosulfur Compliance Markers in a Garlic Extract", J. Agric. Food Chem. 41:37–41.

Weinberg et al., 1993, "Identification and Quantification of Isoflavonoid and Triterpenoid Compliance Markers in a Licorice–Root Extract Powder", J. Agric. Food Chem. 41:42–47.

* cited by examiner

PHARMACEUTICAL GRADE BOTANICAL DRUGS

This is a continuation-in-part of Ser. No. 08/421,993 filed on Apr. 14, 1995, now abandoned.

BACKGROUND OF THE INVENTION

1. Field of the Invention

The present invention relates generally to botanical materials and methods for making such materials in medicinally useful and pharmaceutically acceptable forms. More particularly, the present invention relates to the use of compositional and activity fingerprints in the processing of botanical materials to produce drugs which qualify as pharmaceutical grade compositions which are suitable for use in clinical settings to treat disease.

2. Description of Related Art

Plants have been, and continue to be, the source of a wide variety of medicinal compounds. For centuries, various forms of botanically derived materials have been used to treat countless different ailments. The botanical materials have typically been in the form of powders made from of one or more plants or plant parts or extracts derived from whole plants or selected plant parts. These powders and extracts are for the most part complex mixtures of both biologically active and biologically inactive compounds.

Although plant powders and extracts have been used widely for medicinal purposes, there a number of problems associated with the use of such medicaments. For example, the complex and unknown chemical nature of the botanical materials makes it difficult, if not impossible, to use the botanical materials in any type of controlled and predictable manner. The potential variations in the chemical composition of different batches of material obtained from different plant harvests makes such materials unsuitable for use in clinical situations.

On a positive note, the complex groupings of bioactive ingredients typically found in botanical materials presents the potential for synergistic bioactivity profiles. However, these potential increases in medicinal effectiveness are not predictable due to the unknown nature of these complex materials.

The above problems associated with the inherent chemical complexity of botanical medicaments has resulted in a great deal of effort being directed to the separation and isolation of the biologically active ingredients from numerous medicinally important botanical materials. This area of endeavor has expanded rapidly in conjunction with the many improvements in chemical separation and analysis technology. Once isolated and purified, the various active ingredients are used in clinical settings to establish the medicinal effectiveness of the specific ingredient. Separation and purification of individual ingredients from botanical materials is the cornerstone of this type of drug development procedure. Once purified, the suspected active ingredient is typically mixed with a pharmaceutically acceptable carrier and subjected to further studies in laboratory animals and eventual clinical trials in humans. Upon proof of clinical efficacy, these types of drugs are considered to be pharmaceutical grade because they contain a single or at most small number of well-characterized compounds which are present in known quantities.

Pharmaceutical grade drugs are advantageous in that they allow careful tracking of the effects of individual compounds in treatment protocols. Further, the dosage of the drug can be carefully controlled to provide relatively predictable medicinal action. A disadvantage of the relative purity of such pharmaceutical grade drugs is that the potential for complex and synergistic biological activity provided by naturally occurring plant extracts is reduced because of the isolation of the drug from its natural environment. The potential benefit provided by such synergistic activity is believed by many industry experts to be outweighed by the clinical risks associated with the use of complex plant extract mixtures which are not well characterized or controlled and whose use in a clinical setting is unpredictable.

Although isolation and purification of single compounds from plant materials has been a popular form of drug research and development, there also has been interest in studying complex botanical extracts to characterize their medicinal qualities. For example, as discussed below, mistletoe extracts have been studied in some detail.

Mistletoe belongs to the genus Viscum (family, Loranthaceae) which includes a variety of semiparasitic plants found all over the world. Mistletoe is a parasite which grows on a variety of deciduous trees including apple, cherry, oak, ash hawthorn, lime and acorn. Mistletoe and extracts of mistletoe have been used for centuries in a wide variety of therapeutic settings. The effectiveness of mistletoe as a remedy for treating a multitude of ailments has been the subject of a great deal of folklore, superstitions and mystical accounts. Although many of the early uses for mistletoe may have been based more on fantasy than on fact, the reputation of mistletoe as a powerful elixir is well deserved because this parasitic plant contains a rather large variety of complex and pharmacologically potent ingredients.

Beginning in the early 1900's, mistletoe and the pharmacological properties of extracts from mistletoe have been subjected to a more rigorous scientific investigation. In particular, mistletoe extracts have been suggested for use in treating a variety of specific diseases including cardiovascular illnesses, especially hypertension and arteriosclerosis; cancer and arthrosis. Fermented mistletoe extracts marketed under the tradenames ISCADOR®, HELIXOR® and PLENOSOL® have been proposed for use in treating a number of specific diseases. ISCADOR® and HELIXOR® have been injected subcutaneously while PLENOSOL® has been administered both intracutaneously and intravenously. These three commercially available preparations are derived from mistletoe found in Europe, *Viscum album L.*

Since 1980, the investigation of mistletoe has increased due to its immunomodulatory properties and potential usefulness in treating HIV and cancer. See International Journal of Cancer Research Treatment—ONCOLOGY—Vol. 43, Supplement 1, 1986. A major problem facing mistletoe investigators has been the analysis, identification and standardization of the pharmacologically active ingredients in mistletoe and extracts thereof. This problem is exacerbated by the fact that the numerous complex ingredients which are found in mistletoe extracts vary widely in type and amount depending upon the species of mistletoe, the location where the plant is grown, the time of year when the plant is harvested, the particular host tree, the extraction procedure used and a number of other factors.

The principal classes of ingredients in mistletoe which have been found to provide pharmacological activity include lectins, phenylpropans, viscotoxins, alkaloids, flavonoids, lignans, amines, phenyl carboxylic acids and polysaccharides. Although the general classes of pharmacologically important compounds which are generally present in mistletoe have been identified, investigators have not had a great deal of success with respect to standardizing the multitude of available extracts to establish if one or more ingredients are responsible for the observed bioactivity and whether the specific ingredients act together or may be effective individually. The extremely diverse nature of mistletoe extracts and the inherent variability in extract compositions makes it difficult to use the extracts to conduct clinical investigations.

The preceding discussion regarding mistletoe is exemplary of the state of the art with respect to the plant materials which have been studied in detail. Many other complex plant materials and extracts exist which have potent, but relatively unpredictable, medicinal properties. These manufactured materials are, for the most part, useless in a clinical setting because of the inherent risks involved with treating patients with poorly characterized materials which have no established batch consistency and which may differ widely in composition. Accordingly, there is a need to provide methods for standardizing such complex materials so that they may be used more effectively in clinical research and patient treatments.

SUMMARY OF THE INVENTION

In accordance with the present invention, a method is provided for making pharmaceutical grade botanical drugs. The term "pharmaceutical grade" when used in this specification means that certain specified biologically active and/or inactive components in the botanical drug must be within certain specified absolute and/or relative concentration limits and/or that the components must exhibit certain activity levels as measured by a given bioactivity assay. The pharmaceutical grade botanical drugs made by the method of the present invention are particularly well-suited for use in clinical studies and treatment of patients in general. The method insures that the drug being used as the basis for a particular treatment protocol will be effective for its intended purpose.

The method of the present invention involves processing a biological material to produce a composition which qualifies as a pharmaceutical grade drug by meeting certain requirements with respect to the quantity of specific ingredients (i.e. quantitative fingerprint) and the biological activity of the material with respect to one or more biological assays (i.e. biological fingerprint). Initially, a sample of the botanical material of interest is obtained. The material, if necessary, is processed to form an extract or other composition which is intended for use as a drug. The processed material may include a plurality of active ingredients which exhibit a given biological activity and plurality of inactive ingredients which do not directly exhibit the biological activity of interest. An aliquot is removed from the botanical material and subjected to quality assurance or standardization assay. The assay involves separating the aliquot of processed material into a plurality of marker fractions wherein each of the marker fractions includes one of the active ingredients or one of the inactive ingredients. The amount of active ingredient or inactive ingredient in each of the marker fractions is determined in order to provide a quantitative fingerprint of the aliquot. The degree of biological activity for each of the marker fractions is also determined to provide a biological activity fingerprint for the aliquot. The quantitative and biological activity fingerprints of the aliquot are then compared to corresponding fingerprints which have been established for a pharmaceutical grade drug. If the fingerprints of the processed botanical material match the standard fingerprints, then the material is identified as a pharmaceutical grade botanical drug. If not, then the material is modified so as to provide a match with the standard fingerprints.

The method of the present invention is well-suited for use in preparing a wide variety of botanical drugs which can be used in clinical settings for research and general patient treatment. The present invention provides the ability to closely control the quality, dosing and clinical effectiveness of botanical extracts and other material. One aspect of the present invention involves the establishment of the compositional and/or bioactivity fingerprint standards for various botanical materials. Once established, the fingerprint standards are used in drug production procedures to insure that the botanical extracts meet pharmaceutical grade requirements. Specific quantitative and biological fingerprints are presented which have been established for a number of botanical materials as a further aspect of the invention. These fingerprints are useful for determining if a particular botanical material meets levels of pharmacological activity and composition requirements for a particular treatment regimen. Such a determination is important to insure that clinical studies and patient treatment with the botanical materials are based on consistent and verifiable extract composition parameters.

The above discussed and many other features and attendant advantages of the present invention will become better understood by reference to the following detailed description when taken in conjunction with the accompanying drawings.

DETAILED DESCRIPTION OF THE INVENTION

The present invention is a method for producing botanical drugs which may be classified as being of pharmaceutical grade. As mentioned briefly above, "pharmaceutical grade" means that certain specified biologically active and/or inactive components in the botanical drug must be within certain specified absolute and/or relative concentration limits and/or that the components must exhibit certain activity levels as measured by a given bioactivity assay. In one embodiment, the drug has been fully characterized with respect to the quantity of each significantly active ingredient in the drug and the biological activity of the drug In certain selected assays. This invention is useful in providing botanical materials which are sufficiently characterized and, whose compositions are consistent between batches, so that they can be precisely dosed and used effectively in clinical settings.

The examples of different types of botanical materials which may be processed in accordance with the present invention include all of the many different varieties of mistletoes, coriolus versicolor, saw palmetto berry, Echinacea (purple cornflower). Similar methods are to be used to process other botanicals such as garlic, St. Johns wort and fenugreek. The botanical material is preferably processed to form an aqueous or organic extract of the whole plant or a selected part of the plant. The biological material can also be processed in whole or part to form a powder. In general, extracts of the plant material are preferred because they are easier to dissolve in liquid pharmaceutical carriers. However, powdered plant materials are well-suited for many applications where the drug is administered in solid form, eg. tablets or capsules.

The present invention involves two basic procedures. The first procedure, as schematically outlined in FIG. 1, involves establishing what the compositional and bioactivity fingerprint standards should be for a given pharmaceutical grade botanically derived drug. Once the fingerprint standards are established, then the actual processing of botanical materials into pharmaceutical grade drugs can be carried out as schematically outlined in FIG. 2.

Figure 1:
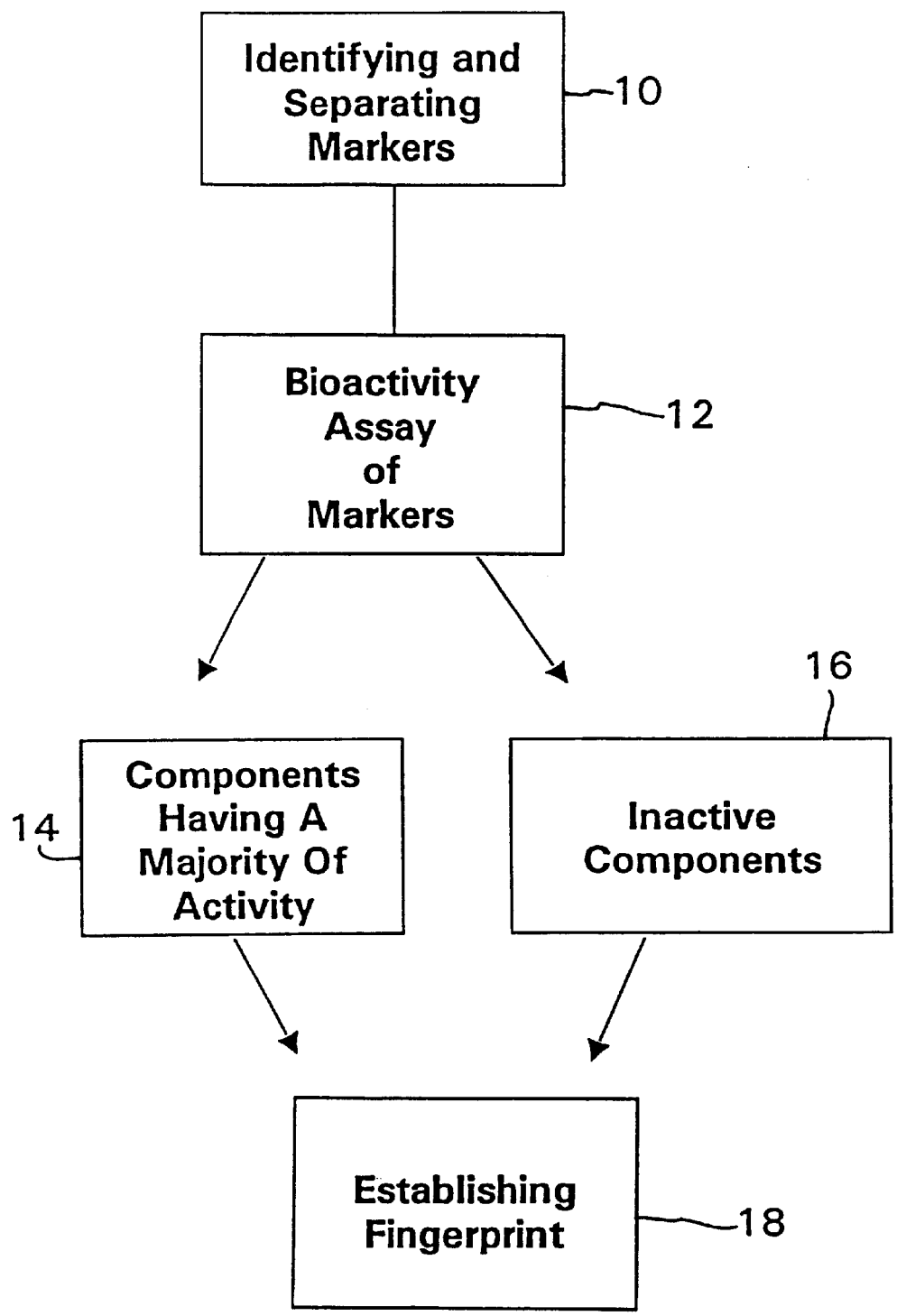
FIG. 1 is a schematic representation of a procedure in accordance with the present invention which is used to establish standard compositional and bioactivity fingerprints against which subsequent processed biological materials are compared during production of pharmaceutical grade drugs.

The initial step in establishing the compositional and bioactivity fingerprint for a given processed biological material involves separating the extract or powder into one or more groups as represented by step 10 in FIG. 1. These groups are separated out and identified based on their potential as markers for the fingerprint which is to be established for the processed biological material. The compounds or groups of compounds which are chosen and identified as the markers will vary widely depending upon the biological material being processed and the pharmaceutical use for the material. There should be at least two markers selected for each processed biological material. The number of markers is preferably more than five and can be as high 15 to 20 or more for complex biological extracts or powders. The markers are identified and selected, for the most part, based on their potential biological activity or contribution to biological activity for a given pharmaceutical application. Markers which have no apparent biological activity by themselves may be separated out and included as markers for use in the fingerprint especially where the markers' presence is required in order to provide an overall observed biological activity for the botanical drugs.

The initial separation of the processed biological material into various groups of markers is accomplished by conventional separation techniques ranging from simple extraction to complex affinity and gel filtration chromatography. Once the markers have been identified for a given material, then the bioactivity of each of the markers is determined as depicted by step 12 in FIG. 1. The particular bioassay used to determine bioactivity of the material is chosen based upon the intended use for the material. The bioassay preferably will provide a reflection of the markers bioactivity with respect to the condition which is to be treated with the material.

The bioassay results obtained in step 12 are used to identify the components having the desired bioactivity (step 14) and those which are less active or essentially inactive (step 16). Each of the groups identified in steps 14 and 16 are then analyzed quantitatively to determine the amount of material present in each group. The results of the bioassays and quantitative compositional assays are then used to prepare a bioassay fingerprint and a quantitative fingerprint for the processed biological material as depicted by step 18 in FIG. 1. As part of establishing the fingerprints for the material, acceptable ranges of bioactivity and quantitative composition are determined. This is done primarily based upon establishing acceptable ranges of bioactivity and quantitative amounts for each marker which provides desired pharmacological activity for the processed material as a whole. Various combinations of active and inactive marker compounds are evaluated to establish potential increases in desired bioactivity resulting from combinations of the active and inactive ingredients. In addition, various combinations of active and inactive markers compounds are evaluated to establish possible potentiation of toxic side effects. In many cases, one or more active or inactive marker compounds are required in combination with highly active marker compounds to alleviate the high toxicity of the active marker compound when administered alone.

The bioassay and quantitative fingerprints which are established in step 18 provide an accurate identification of the processed biological material which can be used in establishing the dosage regimens and treatment schedules which are necessary for clinical use. The dosage regimens and treatment schedules are established using conventional clinical methods which are commonly employed when investigating any new drug. The processed material which is used to determine the dosage and treatment schedules must be matched with and meet the requirements of the fingerprints established in step 18. This insures that the dosage and treatment schedules are effective and reproducible since the processed materials used in the dosage and scheduling studies all have the same fingerprints in accordance with the present invention.

The bioassay and quantitative fingerprints which are determined by the general procedure as set forth in FIG. 1 are used as part of the manufacturing procedure for producing pharmaceutical grade biologically processed materials. The fingerprints are used as part of a quality assurance or standardization procedure to insure that a given biological material contains the appropriate compounds and is processed correctly to provide a processed biological material which will perform the same clinically as the material which has been standardized and tested in accordance with the procedure set forth in FIG. 1.

Figure 2:
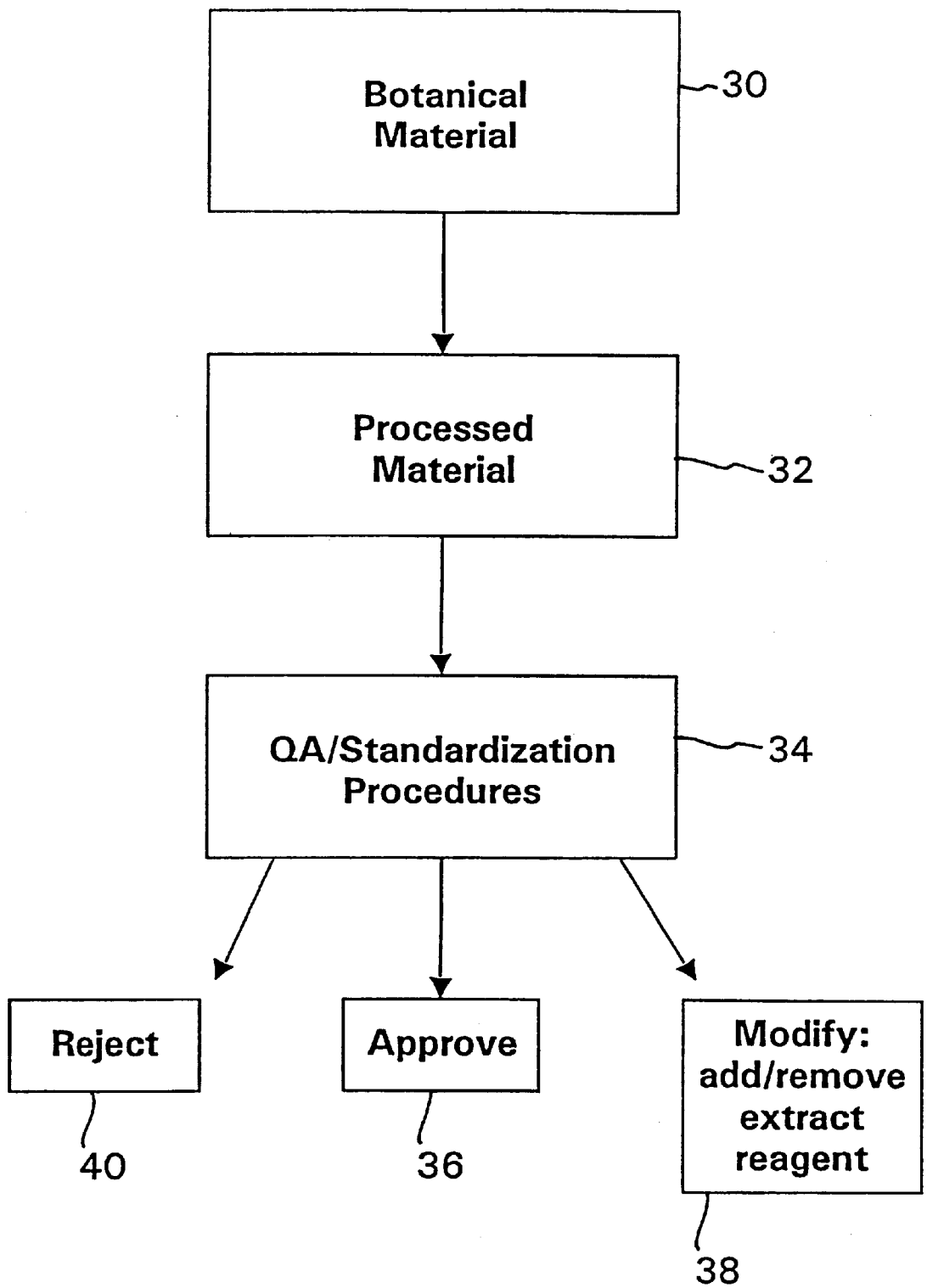
FIG. 2 is a schematic representation of a procedure in accordance with the present invention which is used to process biological materials into pharmaceutical grade drugs.

An exemplary procedure for producing pharmaceutical grade materials in accordance with the present invention is shown schematically in FIG. 2. The botanical material of interest 30 is first processed by extraction, powdering or other manufacturing process to form a processed biological material 32. A sample of the processed material 32 is then analyzed to establish whether or not it matches the fingerprint requirements established during the standardization procedure of FIG. 1. This quality assurance or standardization procedure is depicted at 34 in FIG. 2. If the processed material meets the previously established fingerprint requirements for the particular material, then it is approved as being of pharmaceutical grade as represented by step 36. If the material is close, but does not quite match the standard fingerprint, then it is modified as required to match the fingerprint standards (step 38). The modification of the processed material to meet fingerprint standards may be done by further extraction of the material, if necessary, or the addition of various compounds, as required. If the processed material is substantially outside the fingerprint ranges for both bioactivity markers and quantitative markers, then the batch is rejected (step 40).

The quality assurance or standardization step 34 used to determine if a given processed botanical material is pharmaceutical grade involves obtaining a homogeneous sample or aliquot of the processed botanical material which is to be tested. The homogeneous sample should include the marker compounds which contribute to the observed biological activity of the material and produce the bioactivity and quantitative fingerprint of the previously determined standard. The sample will also include one or more inactive ingredients. Inactive ingredients are those which do not have a direct measurable biological activity, but which are present in the botanical material and may be one or more of the marker groups which makes up the standard fingerprint. The sample is preferably only a small aliquot of the botanical material being tested. Accordingly, it is important that a homogeneous sample be obtained which is representative of the entire batch of material.

The sample or aliquot is separated into the same plurality of marker fractions which are present in the standard fingerprint. Each of the marker fractions will include one or more of the active or inactive ingredients. The marker fractions are established on an individual basis for each botanical material being tested. For some materials only a few marker fractions are required. For other more complex materials, there may be numerous marker fractions. For example in *Viscum album* protein extract, the preferred protein marker fractions are those fractions which are separated based on the sugar binding affinity of the fraction. However, different parameters for identifying and separating the materials into the marker fractions may be established based upon the types of ingredients present in the botanical material. Separation of the sample into the marker fractions may be accomplished by any of the conventional separation techniques including liquid chromatography and extraction procedures. The same procedures which were used to establish the standard fingerprints should be used. Since the various fractions are to be tested for biological activity, it is preferred that non-destructive separation techniques be utilized. Liquid column chromatography is the preferred separation technique with affinity chromatography based on the specific binding ability of the compounds (e.g. carbohydrates and target enzymes) being particularly preferred.

Once the sample is separated into individual marker fractions, each fraction is analyzed to determine the amount of ingredient therein and provide a quantitative fingerprint of the sample. The quantitation of each fraction can be achieved using any of the known quantitative analysis methods. Exemplary quantitation methods include gravimetric analysis, spectral analysis or the use of quantitative detectors, such as those used in gas chromatography and other separation systems. Other suitable quantitative analytical methods include protein estruation by color reaction and polysaccharide color, fluorescent methods, anti-body assay (ELISA).

The results of the quantitative analysis of each fraction are used to prepare a quantitative fingerprint of the sample. The fingerprint is composed of the quantity of ingredient in each of the marker fractions and the identity of the ingredient. This quantitative fingerprint is then compared to the known standard fingerprint which has been established (FIG. 1) in order for the material to be considered as pharmaceutical grade. If the quantitative fingerprint of the sample falls with the range of quantities set forth for the pharmaceutical grade fingerprint, then the material is provisionally identified as being of pharmaceutical grade.

As a further and essential part of the quality assurance assay, the individual marker fractions are subjected to biological assays. The biological assays which are used to test the various fractions are the same as those used for the standard fingerprint and will also depend upon the particular clinical use intended for the material. Exemplary biological assays include any cell proliferation assays, such as the measurement of L1210 cell inhibition, immune activity or inhibition of critical enzyme which relates to specific diseases. Examples of other transformed cell lines which can be used for bioassays include HDLM-3 Hodgkin's lymphoma and Raji Burkitt's lymphoma.

The results of the biological assays are used to prepare a bioactivity fingerprinting of the material. The fingerprint can be as simple as an assay of two selected marker fraction. Conversely, the fingerprint can include numerous different bioassays conducted on numerous different fractions. The same assay may be conducted on different marker fractions. Also, different assays may be conducted on the same marker fraction. The combination of bioassays will depend upon the complexity of the given botanical material and its intended clinical use. The bioassays will be the same as those conducted in establishing bioactivity fingerprint of the standard material.

The bioactivity fingerprint generated for the material is compared to the standard bioactivity fingerprint which has been established in order for the material to be considered as pharmaceutical grade. If the bioactivity fingerprint of the sample falls within the range of bioactivities set forth for the pharmaceutical grade fingerprint, then the material is identified as, and approved as, being of pharmaceutical grade.

Examples of practice of the invention showing the establishment of standard fingerprints (FIG. 1) against which later processed biological materials are compared to verify that they are pharmaceutical grade are as follows:

EXAMPLE 1

Pharmaceutical Grade Mistletoe Extracts

The following example sets forth the general production of pharmaceutical grade extracts of mistletoe which are effective in the treatment of AIDS and certain cancers. Initially the extract was separated into different classes of its chemical entities (components). It was found that the major biological activity was associated with its protein fraction (>95%) and the residual activity was separated in the alkaloid fraction (see FIG. 4). The quantitative fingerprint is based on the measurement of specific protein fractions which have different binding affinities for various sugars. The standard pharmaceutical grade quantitative fingerprint requires that the fractions contain between 0.01 and 1.0 mg/ml of $Ca^{++}$ dependent sugar-binding proteins which are capable of binding with lactose, galactose, melibiose, N-acetyl-D-galactosamine or fucose and exhibit an inhibitory concentration of below about 0.50 $\mu$g/ml. "Inhibitory concentration", as used in this specification is a measure of the sugar-binding protein's ability to inhibit the in vitro growth of certain cancerous cell lines. The inhibitory concentration is expressed in $\mu$g of sugar-binding protein per ml of extract solution which is required to cause a 50% inhibition of the growth of a particular cancerous cell line. The preferred cell line which is used to measure inhibitory concentrations is a leukemia cell line identified as L1210. This particular cancerous cell line is available from a number of commercial sources. L1210 cells have been used in the past as a screening system for testing drug efficacy. Details regarding the culturing and growth of L1210 cell is described in a number of scientific articles including ONCOLOGY, Vol. 43/S1/86 at pages 42–50 and Experientia 36 (1980) pages 599–600. Other cell lines which can be used to determine inhibitory concentrations include KB cells or other rapidly growing cell lines which demonstrate repeatable results. Other parameters like inhibition of macromolecule synthesis in a given cell culture line may be used.

Identification of the mistletoe extract as pharmaceutical grade, preferably requires that the standard fingerprint of the extract must also contain one or more $Ca^{++}$ non-dependent sugar-binding protein fractions which are capable of binding with lactose, galactose, melibiose, N-acetyl-D-galactosamine or fucose. The quantitative level of the $Ca^{++}$ non-dependent sugar-binding proteins must be between about 0.1 and 2.0 mg/ml for each fraction. The inhibitory activity of the one or more $Ca^{++}$ non-dependent sugar-binding protein fraction is preferably below about 0.5 µg/ml.

The mistletoe powder (processed biological material) is prepared according to any of the known powdering procedures. Any type of mistletoe may be used, however, to maintain the rejection rate of extracts at a low level, it is preferred that the mistletoe extract be prepared from the *Viscum album, coloratum* species which is found on oak trees in South Korea or the *Viscum album L.* species which is commonly found throughout Europe. Further, it is preferred that the mistletoe be flash frozen shortly after harvesting and then ground to a powder in the frozen state. Flash freezing with liquid nitrogen or similar cryogenic liquid is preferred. The entire mistletoe plant may be used in preparing the powder. The preferred harvesting time is when the berries are ripe. Due to the variable and relatively unknown nature of all of the complex ingredients in mistletoe, it is preferred that all of the above listed preferred steps be followed in order to optimize the number of extract preparations which meet the requirements of the method of the present invention. The fresh soft part of the mistletoe plant (including leaf, stem and/or berries) may be pressed to squeeze the cell-sap, which on dilution with water or sterile physiological saline will provide an aqueous extract.

The mistletoe powder is extracted using a substantially pure aqueous solution. The extracting solution may include additional ingredients to enhance the extraction process. The extract may include a salt such as calcium chloride or sodium chloride in an amount sufficient to enhance extraction of proteins from the mistletoe sap. Salt concentrations on the order of 0.02 M are preferred. Detergents such as TRITON® x-100 may also be added to enhance extraction of protein from the plant cell walls. The extractant is preferably buffered with 0.02 M Tris to a pH of about 7.8. The extraction procedure should utilize an amount of extractant relative to the amount of mistletoe being extracted which will produce levels of proteins as set forth below. Preferably, between about 100 and 400 grams of mistletoe powder will be extracted with between about 1000 and 4000 ml of aqueous solution. The powder is mixed in the solution and left to stand for from one to four hours. The powder particulates remaining after the extraction period are separated by filtration, centrifugation or other conventional separation technique to produce the aqueous mistletoe extract.

The mistletoe extract, prior to pharmacological analysis of its contents, is preferably assayed for its overall biological activity. The biological evaluation of the extract is carried out on the basis of its inhibition of the growth of mouse leukemia L1210 in culture. From this initial test, the $ID_{50}$ (concentration in $\mu$g/ml of the extract which will cause 50% inhibition in the growth of L1210 cells as compared to untreated controls) of the extract is determined. The biological activity of the extract is expressed in terms of "activity units" (A.U.), which represent ratio of concentration of the extract (expressed in $\mu$g extract/ml) to its $ID_{50}$ value ($\mu$g/ml). To pass this initial step of extract evaluation, 1 ml of 1% extract (10 mg total extract) must contain 100 or more activity units. Extracts with lower than 100 A.U. values are rejected, and those with a passing grade are further analyzed to established specific values and ratios of its biologically active components as described below.

The separation of the mistletoe extract into its various protein fractions is preferably conducted by affinity column chromatography as schematically represented in FIG. 3. The separation is preferably conducted in two stages in order to separate the proteins which require $Ca^{++}$ for binding to sugar and those proteins which are non-$Ca^{++}$ dependent. A Buffer which contains ethylene diamine tetraacetic acid (EDTA) or other chelating agent is used to elute the $Ca^{++}$ dependent sugar-binding proteins from affinity columns which have been treated with the specific sugars of interest, i.e. lactose, galactose, melibiose, N-acetyl-N-galactosamine and fucose. The resulting fractions are then analyzed for quantitative protein content. Other affinity columns based on similar principles of chromatography may also be used, e.g. mannose, rhamnose, maltose, asialofeutin, glucosamine and n-acetyl glucosamine. The appropriate levels and activities of the lectins in the extract which are specific for these sugars can be established by measuring their levels in extracts which meet the criteria for sugar-specific lectins set forth above.

After elution of each of the sugar-specific affinity columns with EDTA or EGTA (ethylene glyceryl tetracetic acid)-containing buffer, the columns are then eluted with buffers that each contain the sugar which corresponds to the sugar bound to the respective affinity columns. Sepharose® 4B is a preferred column material. The various fractions resulting from this second elution contain the non-$Ca^{++}$ dependent sugar-binding proteins. The protein content of each of these fractions is also quantitatively determined. Protein quantitation can be performed using any of the conventional quantitative analytical procedures including ninhydrin based tests, spectroscopic determination and Bio-Rad or Pierce analysis. The use of multiple buffers as described above is preferred so that the total level of each type of protein is determined. Affinity column chromatography is preferred because it is a conventional separation technique which is well-known to those of ordinary skill in the art and which is well-suited for separating the proteins from the extract based on their sugar-binding specificity. Other separation procedures may be utilized provided that an accurate measurement of each of the selected sugar-binding proteins is provided.

An alternate method for analyzing the lectin (sugar-binding protein) content, alkaloidal fraction and viscotoxin levels in the extract involves the use of ammonium sulfate. In this method, the total proteins of mistletoe preparation is precipitated with 70% ammonium sulfate. The preparation is centrifuged and the precipitate which contains a mixture of the viscotoxins and the sugar-binding proteins (lectins). This mixture is separated on a acid-hydrolysed Sepharose 4B column. The bound lectins can be eluted from the column with buffers containing specific sugars as described above. Affinity chromatography to identify the specific sugar-binding proteins can be carried out as also described above. The unbound proteins which initially fan through the column contain viscotoxins which are quantitated according to conventional protein quantitative analysis.

The ammonium sulfate-supernatant, which contains the alkaloidal fraction, is lyophilized and the alkaloids are extracted with chloroform. The chloroform residue provides the total alkaloids which are also quantitated by weighing or conventional method.

The five $Ca^{++}$ dependent and non-$Ca^{++}$ dependent sugar-binding protein fractions which are used to generate fingerprints are those that bind with lactose, galactose, melibiose, N-acetyl-D-galactosamine or fucose. The concentration of each of the sugar binding proteins (both $Ca^{++}$ dependent and non-$Ca^{++}$ dependent) is between 0.1 and 2.8 weight percent of the total protein content of the extract. The specific relative weight percent ranges which are necessary for an extract to meet the requirements of the present invention are set forth in Table 6. Tables 7 and 8 set forth the weight percent ranges for pharmaceutical grade extracts prepared from European and Korean mistletoe, respectively.

The relative percentage of each sugar-binding protein with respect to the total protein content of the extract will remain fairly constant irrespective of extraction conditions. However, the actual concentration levels of the various sugar-binding proteins will vary in each extract depending upon a number of factors including the relative amounts of mistletoe and aqueous extractant, the length of extraction and temperature. It is preferred that the extract be analyzed to determine the concentration levels of the various specified sugar-binding proteins and that these concentration levels be used as the primary method of determining whether an extract meets the pharmaceutical grade requirements of the present invention. However, the extract may be diluted or concentrated to achieve protein concentration levels outside the preferred concentration ranges provided that the relative percentages of the sugar-binding proteins remain within the limits set forth in Table 6, for general mistletoe extracts, and Tables 7 and 8 for European and Korean mistletoe extracts, respectively. The extract, once it has been identified as pharmaceutical grade, may be dehydrated, and stored as a powder for rehydration and use at a later time to treat AIDS or cancer.

The preferred concentration level of the $Ca^{++}$ dependent sugar-binding proteins in the extract is within the range of about 0.01 to 1.0 mg/ml. The method of the present invention can be carried out by measuring only one of the $Ca^{++}$ dependent sugar-binding proteins to establish if the extract is within pharmaceutical grade limits. However, it is preferred that two or more of the sugar-binding protein levels be measured, e.g. galactose, lactose and/or N-acetyl-D-galactosamine specific proteins. Even more preferably, the extract is analyzed to determine if the concentration levels of all five $Ca^{++}$ dependent sugar-binding proteins meet the above quantitative fingerprint limits. The method can also be carried out by measuring various combinations of 3 or 4 of the specified $Ca^{++}$ dependent sugar-binding proteins. Concentration ranges and inhibitory activity ranges are set forth in Tables 9, 10 and 11.

The concentration level of the non-$Ca^{++}$ dependent sugar-binding proteins in the extract must be within the range of about 0.10 to 2.0 mg/ml. The method of the present invention can be carried out by measuring only one of the non-$Ca^{++}$ dependent sugar-binding proteins to establish if the extract is within pharmaceutical grade limits. However, as above, it is preferred that two or more of the non-$Ca^{++}$ dependent sugar-binding protein levels be measured. Even more preferably, the extract is analyzed to determine if the concentration levels of all five non-$Ca^{++}$ dependent sugar-binding proteins meet the required concentration limits. The most preferred method involves determining the complete protein finger print, i.e. the protein concentration in all ten sugar-binding protein fractions. In this most preferred embodiment, the extract is not identified or otherwise considered to be a pharmaceutical grade extract unless all ten protein fractions have the required concentration levels set forth above. The standard fingerprint parameters are set forth in Tables 9, 10 and 11.

The bioactivity of the various protein fractions are used in combination with their respective concentration levels to identify the extract as pharmaceutical grade in accordance with the present invention. The various proteins which make up each of the $Ca^{++}$ dependent sugar-binding protein groups must each exhibit an inhibitory concentration of between about 0.001 and 0.5 $\mu$g/ml. The proteins which make up each of the non-$Ca^{++}$ dependent sugar-binding groups must also each exhibit an inhibitory concentration of between about 0.0001 and 0.5 $\mu$g/ml.

The method for measuring inhibitory action is set forth in numerous scientific articles including the references mention previously. It is preferred that the inhibitory action be measured in vitro with respect to leukemia L1210 cells. This procedure is preferred because L1210 cells are readily available, they are easily maintained by well-known culturing procedures and provide consistently reproducible results. The inhibitory concentration of each sugar-binding protein fraction is determined by adding increasing amounts of the fraction and determining when cell growth is inhibited by 50% as compared to a control culture. It is preferred that both the concentration level and the inhibition concentration of each of the sugar-binding proteins be measured and that they all be within the ranges set forth above and in Tables 9, 10 and 11 in order for the extract to be identified as pharmaceutical grade in accordance with the present invention.

Once the concentration levels and/or inhibitory concentration of the designated sugar-binding proteins has been established, the extract is either identified as pharmaceutical grade if the above limits are met. If one or more requirements are not met (i.e. the sample fingerprint does not match with the standard fingerprint), the extract is rejected. The extracts which are identified as pharmaceutical grade are then used in treatment programs for treating diseases such as AIDS and cancer. The pharmaceutical grade extracts are not only useful in treating AIDS, but they may be used to treat any individual with a suppressed immune system. If the extract has protein levels which are above the limits set forth above, the extract may be diluted as required to bring the extract protein concentrations down to the established limits. If the extract protein levels are below the limits, the extract is rejected and not identified as pharmaceutical grade.

It is preferred that the extract be initially screened for overall activity before beginning the more rigorous analysis of the sugar-binding protein fingerprint. It was discovered that extracts which do not meet certain total activity levels will also not meet the more specific protein fingerprint requirements of the present invention. The activity units are determined in the same manner as for the individual protein fraction with the only difference being that the entire extract is being tested. In accordance with the present invention, the extract must have and activity of greater than 100 AU. Table 12 sets forth the results of initial screening wherein a number of different mistletoe extracts were screened to determine their biological activity using the L1210 cells as previously described. As can be seen, commercial preparations, such as ISCADOR, do not meet the initial screening test and therefor are not pharmaceutical grade in accordance with the present invention. The ISCADOR extracts also do not meet the more stringent specific protein fingerprint requirements of the present method. However, the extracts n-T4GEN and T4GEN, which do meet the specific protein concentration fingerprint of the present invention, both have activity levels well above the minimum of 100 A.U. The screening procedure is preferred because it allows non-pharmaceutical grade extracts to be identified relatively quickly without having to conduct the more time consuming protein fingerprinting. Once an extract passes this initial screening step, it then still must meet the further protein fingerprint requirements in order to qualify as pharmaceutical grade in accordance with the present invention.

Figure 3:
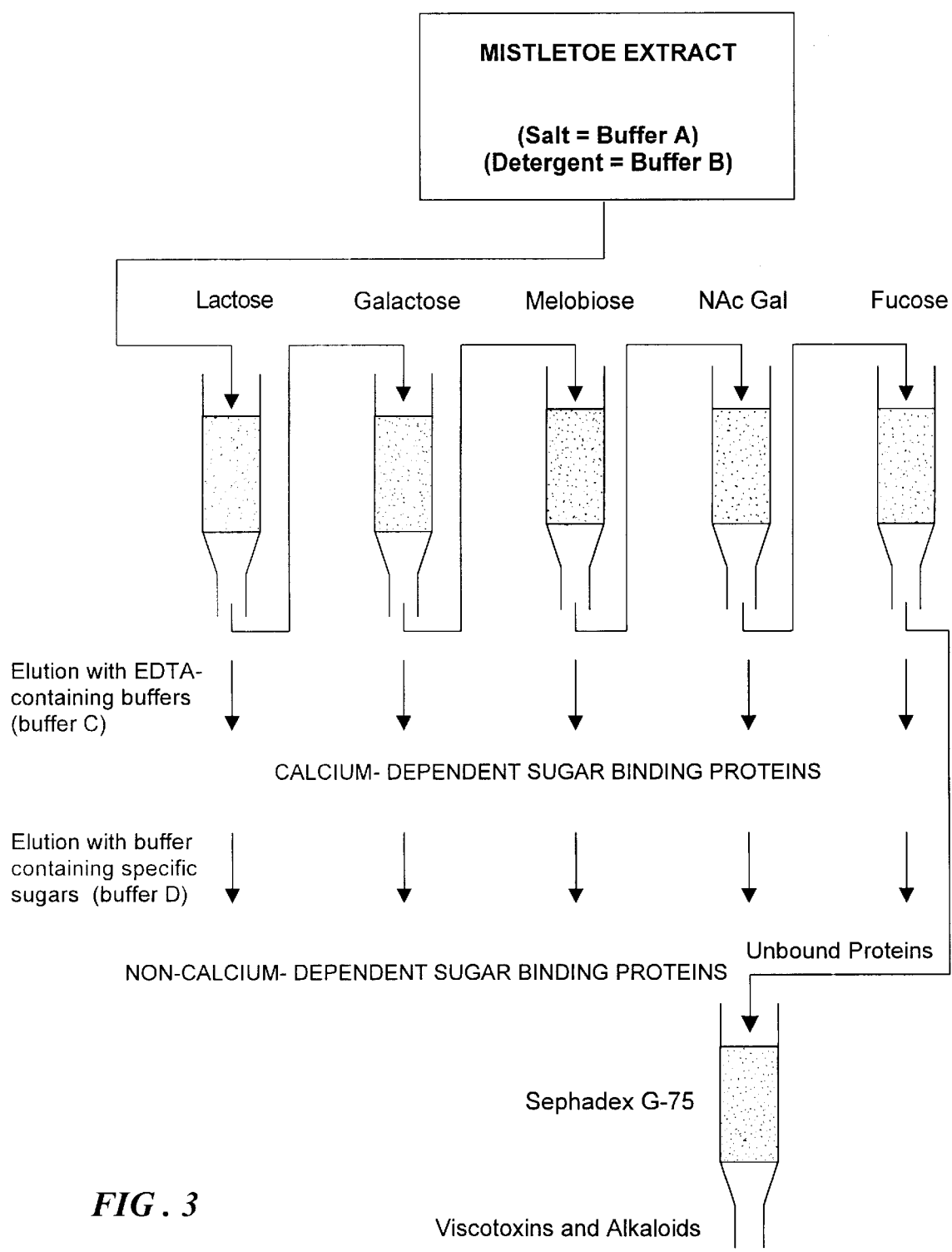
FIG. 3 is a schematic representation of a preferred exemplary extraction procedure which produces an aqueous extract of mistletoe which is analyzed in accordance with the quality assurance method of the present invention.

It is also preferred that the fraction of the extract which contains protein that does not bind to sugar be analyzed to provide a further fingerprint that is used in identifying whether the extract is pharmaceutical grade. As shown in FIG. 3, a fraction containing unbound protein remains after separation of the sugar-binding proteins from the extract. This unbound protein fraction contains an "alkaloid" fraction and a viscotoxin fraction. These two fractions can be isolated from each other by column chromatography using a Sephadex G-75 column or equivalent. The amount of alkaloids in the alkaloid fraction should be about 10 to 50 µg per ml of 1 percent extract. The amount of viscotoxin in the protein fraction should be about 10 to 40 µg per ml of 1 percent extract. As previously described, a 1 percent extract is one where 1 gram of total initial non-dehydrated plant material is extracted with 100 ml of aqueous extractant. The amount of viscotoxins and alkaloids will increase proportionally as the amount of plant material extracted per 100 ml increases.

In use, the extracts may be used as is or diluted with suitable pharmaceutical carriers and administered according to known procedures for treating AIDS or a particular cancer. For treating AIDS, the extract is preferably injected subcutaneously in doses ranging from 0.01 to 1 ml of a 1 percent extract. Extracts which are more concentrated, such as 2 and 5 percent extracts, may be used. Extracts with even higher concentrations may also be used depending upon the dosage required. The injections are preferably given twice a week, but may be given more often. For cancerous tumors, the extract is injected directly into the tumor or may be injected subcutaneously.

An extract identified herein as n-T4GEN was tested to demonstrate its anti-HIV activity. n-T4GEN was analyzed and found to meet the sugar-binding protein fingerprint set forth in TABLE 11. The amount of protein in the alkaloidal and viscotoxin fractions were also found to be within the required fingerprint ranges. The n-T4GEN extract was prepared from Korean mistletoe. n-T4GEN was added to culture wells in an amount sufficient to provide concentration of 1 µl of a 1 percent extract per ml of test solution (equivalent to 10 µg of extract per ml of test solution). This concentration of n-T4GEN inhibited HIV-induced cytopathic effects in H9 lymphoid human leukemia cells with concomitant reduction in viral reverse transcriptase levels in the infected cells.

Human immunodeficiency virus (HIV) infects T4 lymphocytes. In the H9 human lymphoma cell line, the virus produces giant multinucleated syncytial cells. After 3–6 days of viral infection, the number of syncytia correlates with the degree of virus growth as quantified in the presence and absence of the drug being tested. These cytopathic effects and assay of viral reverse transcriptase were used to demonstrate anti-HIV effects of n-T4GEN.

The anti-HIV assay using 1 µl/ml of a 1 percent n-T4GEN extract per ml of test solution was conducted as follows:

HIV inoculum was standardized for reverse transcriptase (RT) activity using purified avian myeloblastosis viral RT (BRL Labs, Gaithersberg, Md.) and used to infect polybrene treated H9 cells at 0.02 RT units of HIV per $2 \times 10^6$ cells. The virus was adsorbed for 2 hours at 37° C. and then the cells were washed twice and resuspended in RPMI 1640 containing 10% fetal bovine serum at $2 \times 10^5$ cells/ml and dispersed in 1 ml aliquots into 24-well plates (Falcon Division, Beckton Dickinson Co., Cockneyville, Md.). Syncytial giant cell formation appeared at 5–6 days post infection, and this cytopathic effect (CPE) was quantitatively measured by dispersing 0.1 ml aliquots into 0.1 ml absolute methanol and enumerating the giant cells microscopically. The inhibition of CPE by antiviral treatment with 1 µl (10 µg) of a 1 percent n-T4GEN extract per 1 ml of test solution was compared to untreated, infected H9 cells.

Reverse transcriptase activity was measured using 1 ml culture aliquots which were clarified at 600×g for 30 minutes, precipitated in 10% polyethylene glycol—0.13 M NaCl at 4° C. for 18 hours, and centrifuged at 600×g for 60 minutes. The pellet was dissolved in glycerol-Tris buffer (50% glycerol, 25 mM Tris HCl pH 7.5, 5 mM dithiothreitol, 15 mM KCl, 0.025% Triton-X, and 0.25 mM EDTA). The RT assay was adapted from the methods of J. Levy et al., Science 225, 840 (1984); D. D. Ho et al., ibid 226, 451 (1984) using a final reaction mixture containing 40 mM Tris-HCl pH 7.8, 2.2 mM dithiothreitol, 10 mM $MgCl_2$, 50 mM KCl, 0.03% Triton-X, 25 µCi $^3$H-thymidine triphosphate (New England Nuclear, Boston, Mass.), and 50 µg/ml poly rA oligo $^{dT}$12-18 (BRL, Gaithersburg, Md.). Background counts were determined using poly dA oligo $^{dT}$12-18 as template and subtracted from the poly rA dT primer cpm to determine the thymidine incorporation specifically due to RT-activity.

The results of the tests are set forth in Table A as follows:

TABLE A

Effect of Mistletoe Extract on the Infectivity of HIV to H9 Lymphoma Cells in Culture

| n-T4GEN* (µg/ml) | Cytopathic Effects (Syncytia cells) Day 5 | Reverse Transcriptase (cpm) Day 10 |
|---|---|---|
| 0.01 | ++ | 97,896 (100) |
| 0.10 | ++ | 77,971 (79) |
| 1.00 | ++ | 85,932 (67.3) |
| 10.00 | ± | 32,128 (32.8) |
| 100.00 | (toxic) | 4,200 |

H9 lymphoma cells growing in RPMI-1640 media containing 10% fetal calf serum were infected with HIV (100,000 RT counts) on day 1 and various concentrations of n-T4GEN extract. On day 5 cells were observed for cytopathic effects (syncytia), and on day 10 assayed for RT activity.
(++) Denotes extensive giant cells, (±) fewer syncytial cell.
*Amounts expressed. as µg of 1 percent extract per ml of cell culture The results show that n-T4GEN at non-toxic concentrations inhibited HIV-induced cytopathic effects on H9 lymphoma cells. At these concentrations (10 µg/ml) there was also a significant (67.2%) inhibition of the viral reverse transcriptase. An extract identified herein as T4GEN was tested along with n-T4GEN to demonstrate their anti-cancer activity. T4GEN was analyzed and found to meet the sugar-binding protein fingerprint set forth in TABLE 10. The amount of protein in the alkaloidal and viscotoxin fractions were also found to be within the required fingerprint ranges. The T4GEN extract was prepared from European mistletoe.

Anticancer activities of T4GEN and n-T4GEN were studied in animals bearing subcutaneous transplants of C3H Mammary adenocarcinoma 16/C. This tumor is maintained as a lung passed tumor in C3H female mice. In this example, tumors ($1 \times 10^6$ cells) were transplanted (S.C.) in 18–20 g B6C3F1 hybrid female mice. On the following day, the tumor bearing animals were randomized and separated into different treatment groups (10 mice per group). There were 15 animals in the control group who received only physiological saline during the treatment periods. The treatments (i.p.) were started 48 hours after the transplants and given for a duration of 14 days (daily single injections). Animals were weighed on days 5, 9 and 14 to assess toxic effects. Tumors were measured on days 21, 28 post transplants and the results are represented as tumor weights using formula $$\frac{l \times w^2}{2}$$

(l=length of tumor, w=width of tumor expressed in mm).

The results set forth below show that the T4GEN extract at a dose schedule equivalent to 1 ml of a 1 percent extract/kg (20 mg/kg), qd (1–14) caused a 98% inhibition in the growth of this tumor. In the same experiment the n-T4GEN (5 mg/kg, qd 1–14) caused 33% inhibition growth of mammary adenocarcinoma 16/C, however, 30% of the treated animals remained tumor free until the termination of the experiment (day 93). This animal model is an accepted model for human breast carcinomas. The results are set forth in Table B as follows:

TABLE B

Effect of T4GEN and n-T4GEN on the Growth of Subcutaneous Transplants of C3H Mammary Adenocarcinoma 16/C in B6C3F1, Female Mice

| Treatments i.p. | ΔWts (g) (day 14) | Tumor Wts (day 21) | Tumor Weight Inhibition % | Tumor Free Animals (day 93) |
|---|---|---|---|---|
| 1. Saline, Controls | +0.21 | 0.27 | — | 1/15 |
| 2. T4GEN* | | | | |
| 1 ml/kg, qd (1–14) | +0.82 | 0.15 | 44 | 0/10 |
| 2 ml/kg, qd (1–14) | −2.12 | 0.01 | 98 | 0/10 |
| 3. n-T4GEN* | | | | |
| .25 ml/kg, qd (1–14) | +1.33 | 0.15 | 44 | 1/10 |
| .50 ml/kg, qd (1–14) | +0.73 | 0.18 | 33 | 3/10 |
| 4. 5-Fluorouracil 98 mg/kg, qd (1, 7, 14, 21) | +1.77 | 0.00 | 100 | 0/6 |

*Amounts expressed as ml of 1 percent extract.

EXAMPLE 2

Preparation of Pharmaceutical Grade Mistletoe Extract from Korean Mistletoe (n-T4GEN)

Plant powder (2.4 Kg) obtained from Korean mistletoe was extracted with 300 ml batches of water in a clean blender. The extract was filtered through cheese cloth lined filter beds to eliminate fibrous and water-insoluble residues, final volume 6.03 liters. Final concentration of the extract was 39.8% (plant weight/volume).

The extract was left at 4° C. for two weeks in absence of air (flushed with nitrogen). At this time additional insoluble residues were deposited. The cold extract was filtered through 0.8μ filters and final sterile filtration was performed with 0.2 micron filters and in sterile environment. The semipurified product was collected in 500 ml sterile vacuum containers and identified as T4GEN. The product samples were found to be pyrogen free. Samples from the flask were removed with a sterile syringe in a laminar flow hood and diluted on the basis that each ml of the sample contains 400 mg of the extract (~40% solution).

The extract samples were analyzed according to the affinity chromatography system schematically shown in the FIG. 3 which was the same system used to establish the standard marker fingerprints. The columns used to separate the proteins were Sepharose® 4B.

The columns were prepared as follows:

Activation of Sepharose 4B: Sepharose 4B (400 ml) was repeatedly washed with double distilled water and filtered on a buchner funnel. The sepharose residue was repeatedly washed with $Na_2 CO_3$ (0.5 M, pH 11) and then suspended in a stirred 2 liter cylinder in 400 ml $Na_2 CO_3$ (0.5 M, pH 11). The cylinder was covered with aluminum foil and to the stirred suspension of Sepharose 4B, divinylsulfone (48 ml, absence of light) was added dropwise over a period of 80 minutes. The reactants were stirred for another 30 minutes at room temperature. Then the resin was filtered on a sintered glass funnel (no touching with hands or paper) with approximately 500 ml of $Na_2 CO_3$ (0.5 M, pH 10, make with $NaHCO_3$). At this time the resin was suspended in 400 ml $Na_2 CO_3$ (0.5 M, pH 10) and used for preparing sugar-specific affinity resins as follows:

Galactose-specific Sepharose 4B: To the activated resin 380 ml (in 5M $Na_2 CO_3$), galactose (38 g) was added with stirring in absence of light. The suspension was stirred overnight and then the suspension was filtered on a sintered glass funnel. To inactivate the reacted activated sepharose, the residue was washed with 0.5 M $NaHCO_3$ (pH 8.5) and then suspended in 350 ml $NaHCO_3$ (0.5 M, pH 8.5) and 14 ml 2-mercaptoethanol. The stirred suspension was maintained at room temperature for 4 hours and then filtered on a sintered glass funnel. The resin was washed with 0.2 M PBS (phosphate buffered saline) and finally suspended in 380 ml 0.2 M PBS and stored at 4° C. along with a few crystals of $NaN_3$.

Lactose-specific Sepharose 4B: The method of preparation was the same as described for galactose. Here 300 ml of activated Sepharose was reacted with 30 g of lactose and the affinity resin was deactivated with 300 ml $NaHCO_3$ (0.5 M, pH 8.5), 12 ml 2-mercaptoethanol and finally suspended in 300 ml of PBS and $NaN_3$ as described in the previous preparation.

N-Acetyl-D-galactosamine-specific Sepharose B: Activated Sepharose 4B (30 ml) was treated with 3 g of N-acetyl-D-galactosamine as described. The reaction was terminated with 30 ml $NaHCO_3$ (0.5 M, pH 8.5) and 5 ml 2-mercaptoethanol. The resin was maintained in 30 ml PBS and a few crystals $NaN_3$ at 4° C.

Fucose-specific-Sepharose 4B: Activated Sepharose (50 ml) was reacted with 5 g fucose. The affinity resin was treated with 50 ml $NaHCO_3$ and 5 ml 2-mercaptoethanol to deactivate the unreacted Sepharose. The resin was maintained in 50 ml PBS and $NaN_3$ as described.

Melibiose-Specific Sepharose 4B: Activated Sepharose 4B (50 ml) was created with 5 g melibiose. The reaction was terminated with 50 ml $NaHCO_3$ and 5 ml mercaptoethanol. The resin was maintained in 50 ml PBS and a few crystals of $NaN_3$ at 4° C.

The same methods can be used to provide columns of different sugar specificity. The used columns were regenerated by elutions with 5 M urea and followed by elution with 0.5 M $NaHCO_3$ (pH 8.5). Prior to use, columns are equilibrated with 0.02 M Tris/HCl buffer (Buffer C).

The Buffers used for Extraction and Affinity Chromatography were prepared as follows:

All buffers made in double distilled water (DD).

A) Tris/HCl (0.02 M, pH 7.8) containing NaCl (0.2 M) dithiothreitol (1 mM) and just use add phenyl methanesulfonyl fluoride (0.01 mM). (Buffer A).

B) Tris/HCl (0.02 M, pH 7.8) containing 0.4 M KCl, 2% Triton x-100, 1 mM dithiothreitol and 0.01 mM phenyl methanesulfonyl fluoride (to be added before use). (Buffer B).

C) Tris/HCl (0.02 M, pH 7.8) containing 1.25 M NaCl, 25 mM $CaCl_2$, 0.05% Triton x-100 and 1 mM dithiothreitol. (Buffer C).

D) Buffer (C) containing 4 mM EDTA instead of 25 mM $CaCl_2$. (Buffer D).

If desired, EGTA may be substituted for EDTA.

A known volume of the mistletoe extract was adjusted to pH 7.8 with 2 M tris-buffer. The solution was absorbed on a series of Sepharose® 4B affinity columns (1.6×7 ml). The columns were washed with excess of (200 ml) of 0.02 M tris-buffer (pH 7.8) containing 25 mM $CaCl_2$ (Buffer C) to remove all unbound proteins (viscotoxins and alkaloids). Then each column was separately washed with tris-buffer (pH 7.8) containing 4 mM EDTA (Buffer D) to elute proteins which require $Ca^{++}$ for their binding to specific sugars i.e. $Ca^{++}$ dependent sugar-binding proteins (100 ml samples). Subsequently, the columns were washed with tris-buffer (Buffer C, 200 ml) and then eluted with the same buffer (100 ml) containing 0.5 M corresponding sugars to remove non-$Ca^{++}$ dependent sugar binding proteins. The unbound proteins were fractionated on a Sephadex G-75 column (2.5×75 cm) to separate viscotoxins from alkaloids. All fractions were dialyzed to remove salts and other buffer ingredients. Each dialyzed fraction was concentrated by Amicon concentrator using DIAFLO ultrafiltration membrane YM10 (10,000 cutoff). Protein concentration was measured by Bio-rad assay with bovine-globulin as a standard (each separated protein may be characterized for its purity and molecular weight by SDS page gel chromatography).

The inhibitory concentration ($ID_{50}$) was determined for each sugar-binding protein as follows:

Leukemia L1210 was maintained in asynchronous logarithmic growth at 37° C. in RPMI 1640 medium supplemented with 10% (v/v) fetal bovine calf serum and 1% (v/v) Pen Strep. The cell population doubling time was 11–12 hours. The cells were passed every 48 hours at $1×10^4$ cell/ml in order to keep the cells in logarithmic stage of growth.

For all growth inhibition studies all stock solutions and dilutions were made with sterile 0.7% NaCl solution. The cell cultures were seeded at $2–5×10^4$ cells/ml in duplicates for each inhibitor concentration in a microtiter plate (0.18 ml/well). The covered microtiter plate was incubated for 48 hours in a humidified $CO_2$ incubator containing 5% $CO_2$ in air. At the end of the incubation period, aliquots of each well were added to a measured volume of isotonic saline and counted in an electronic counter. Because fractions at high concentrations caused rapid cellular fragmentation, the test microtiter plates were routinely checked under a microscope prior to cell number counting so that the results were not compromised. The cell viability was determined by trypan blue exclusion. The results were calculated by plotting percent cell growth inhibition (as compared to the cell density of the saline treated controls) versus log of protein (or specific fraction) concentration which caused 50% inhibition ($ID_{50}$) in cell growth as determined from the graph.

The results of the analysis are shown in Tables 1 and 2 for n-T4GEN salt and detergent extracts prepared in accordance with this example. As can be seen from Tables 1 and 2, the extracts from both the sap and the cell walls of the Korean mistletoe have protein levels and inhibitory activities which all fall within the limits required to be identified as pharmaceutical grade extracts in accordance with the present invention. Accordingly, these extracts may be used in clinical studies directed to cancer or AIDS treatment. They may also be used for routine patient treatment since their quality and efficacy has been established in accordance with the protein fingerprint identifiers as required by the present invention.

TABLE 1

FRACTIONATION OF THE VARIOUS CONSTITUENTS OF V. ALBUM COLORATUM WITH ANTILEUKEMIA - L1210 ACIVITY - n-T4GEN (40 PERCENT EXTRACT)
(Affinity Method, Fractionation of Salt Extract)

| Fraction identity | Protein Content (mg/ml) | Total Volume (ml) | Total Protein (mg) | $ID^a_{50}$ (μg Protein/ml) | Total Activity[b] Units |
|---|---|---|---|---|---|
| Salt Extract Affinity columns eluted with EDTA buffer - $Ca^{++}$ dependent | 7.63 | 350. | 2673 | 0.11 | $2.4 × 10^7$ |
| 1. Lactose | 0.31 | 20 | 6.24 | 0.38 | $1.6 × 10^4$ |
| 2. Galactose | 0.39 | 20 | 7.91 | 0.25 | $3.1 × 10^4$ |
| 3. Melibiose | 0.28 | 20 | 5.44 | 0.20 | $2.7 × 10^4$ |
| 4. N-Acetyl-D-galactosamine | 0.70 | 12.5 | 875 | 0.29 | $3.00 × 10^4$ |
| 5. Fucose Affinity columns eluted with corresponding sugars - non-$Ca^{++}$ dependent | 0.28 | 18 | 5.04 | 0.36 | $1.4 × 10^4$ |
| 1. Lactose | 0.27 | 22 | 5.98 | 0.00027 | $2.2 × 10^7$ |
| 2. Galactose | 1.40 | 9 | 12.60 | 0.0013 | $9.6 × 10^6$ |
| 3. Melibiose | 0.32 | 10 | 3.20. | 0.0034 | $9.4 × 10^5$ |
| 4. N-Acetyl-D-galactosamine | 0.66 | 18 | 11.90 | 0.017 | $7.0 × 10^5$ |
| 5. Fucose Sephadex - G75 (Unbound proteins) Fractions[c] | 1.17 | 15 | 2.59 | 0.019 | $1.3 × 10^5$ |
| I (12–50) | 1.84 | 46 | 84.6 | 0.5 | $1.69 × 10^5$ |
| II (51–70) | 1.22 | 22.5 | 27.45 | 4.0 | $6.8 × 10^3$ |
| III (71–100) | 1.12 | 40 | 44.80 | 2.8 | $1.6 × 10^4$ |
| IV (101–140)[d] | -0- | 50 | -0- | 13.5 | $1.6 × 10^4$ |

[a]inhibitory concentration expressed as μg protein/ml which caused 50% inhibition of the growth of L1210 cells in culture.
[b]Activity unit is defined as dilution factor needed for a specific fraction which when added to L1210 cells caused a 50% cell growth inhibition.
[c]50 ml on column from a total eluate of 325 ml.
[d]31 mg alkaloids obtained from fraction IV.

TABLE 2

FRACTIONATION OF THE VARIOUS CONSTITUENTS OF V. ALBUM COLORATUM WITH ANTILEUKEMIA - L1210 ACTIVITY (40 PERCENT EXTRACT)
(Affinity Method, Fractionation of Detergent Extract)

| Fraction identity | Protein Content (mg/ml) | Total Volume (ml) | Total Protein (mg) | $ID^a_{50}$ (μg Protein/ml) | Total Activity[b] Units |
|---|---|---|---|---|---|
| Detergent Extract Affinity columns eluted with EDTA buffer | 1.68 | 450 | 756 | 0.27 | $2.8 × 10^6$ |
| 1. Lactose | 0.18 | 22 | 4.04 | 0.250 | $1.6 × 10^4$ |
| 2. Galactose | 0.08 | 11.5 | 0.97 | 0.031 | $3.1 × 10^4$ |

TABLE 2-continued

FRACTIONATION OF THE VARIOUS CONSTITUENTS OF V. ALBUM COLORATUM WITH ANTILEUKEMIA - L1210 ACTIVITY (40 PERCENT EXTRACT)
(Affinity Method, Fractionation of Detergent Extract)

| Fraction identity | Protein Content (mg/ml) | Total Volume (ml) | Total Protein (mg) | $ID^a_{50}$ ($\mu$g Protein/ml) | Total Activity[b] Units |
|---|---|---|---|---|---|
| 3. Melibiose | 0.16 | 20 | 3.12 | 0.054 | $5.7 \times 10^4$ |
| 4. N-Acetyl-D-galactosamine | 0.17 | 19 | 3.20 | 0.078 | $4.2 \times 10^4$ |
| 5. Fucose | 0.12 | 6.5 | 0.78 | 0.100 | $0.5 \times 10^4$ |
| Affinity columns eluted with corresponding sugars | | | | | |
| 1. Lactose | 0.35 | 95 | 3.23 | 0.0045 | $2.1 \times 10^6$ |
| 2. Galactose | 0.50 | 15 | 7.50 | 0.0055 | $1.3 \times 10^8$ |
| 3. Melibiose | 0.15 | 12 | 0.61 | 0.0084 | $0.07 \times 10^6$ |
| 4. N-Acetyl-D-galactosamine | 0.62 | 4 | 7.68 | 0.0035 | $2.1 \times 10^6$ |
| 5. Fucose | 0.50 | 10 | 5.10 | 0.0500 | $0.1 \times 10^6$ |
| Sephadex - G75 (Unbound proteins) Fractions[c] | | | | | |
| I (9–35) | 1.58 | 33 | 52.1 | 1.25 | $0.05 \times 10^6$ |
| II (36–55) | 1.36 | 20 | 27.2 | 1.70 | $0.008 \times 10^6$ |
| III (56–120)[d] | -0- | 50 | -0- | 14.00 | $0.002 \times 10^6$ |

[a]Inhibitory concentration expressed as $\mu$g protein/ml which caused 50% inhibition in the growth of L1210 cells in culture.
[b]Activity unit is defined as dilution factor needed for a specific fraction which when added to L1210 cells caused a 50% inhibition.
[c]50 ml on column from a total of 420 ml.
[d]22 mg alkaloids obtained from fraction III.

The protein containing fractions (12–100) with biological activity in L1210 system obtained from Sephadex G75 column (see Table 1) contained a mixture of viscotoxins (1.019 g). The fractions (101–140) were combined and extracted with 3×200 ml) chloroform. The chloroform layer was dried over anhydrous $Na_2SO_4$, filters and the filtrate was evaporated under vacuum to obtain 201 mg of alkaloids (weights of viscotoxins and alkaloids set forth in Table 1 are adjusted to a total of 325 ml for the unbound fraction obtained from affinity columns). Thus 1 ml of the 1 percent extract contained 4.9 $\mu$g lectins; 72 $\mu$g unbound proteins which contains from 10 to 40 $\mu$g of viscotoxins; and 14.3 $\mu$g alkaloids.

EXAMPLE 3

Preparation of Pharmaceutical Grade Mistletoe Extract from European Mistletoe

An extract of European mistletoe (*Viscum album L.*) was prepared and analyzed according to Example 1 except that only the aqueous salt extract was analyzed for its sugar-binding protein fingerprint. The extract is identified as T4GEN. The results of the fingerprint determination are set forth in Table 3. The T4GEN extract meets the requirement of the established standard fingerprint and therefor qualifies as a pharmaceutical grade extract.

Table 4 sets forth the analysis of ISCADOR® which is a fermented mistletoe extract. This fraction meets some but not all of the requirements of the standard fingerprint. For example, the bioactivity of the melibiose and fucose fractions are too low.

Table 5 shows the results of bioactivity assays for the T4GEN and ISCADOR® extracts where the $ID_{50}$ is expressed as the dilution factor needed per ml to cause 50% inhibition of L1210 cells in culture. Table 5 is derived from Tables 3 and 4 and shows the general drop in ISCADOR® activity compared to the unfermented European extract (T4GEN).

TABLE 3

FRACTIONATION OF BIOLOGICALLY ACTIVE CARBOHYDRATE BINDING PROTEINS FROM T4GEN

| Fraction identity | Protein Content (mg/ml) | Total Volume (ml) | Total Protein (mg) | $ID^a_{50}$ ($\mu$g Protein/ml) | Total Activity Units[b] |
|---|---|---|---|---|---|
| T4GEN (10%, FrF) | 0.9 | 100 | 90 | 0.32 | $4.6 \times 10^5$ |
| Affinity columns eluted with EDTA buffer ($Ca^{++}$ dependent sugar-binding proteins) | | | | | |
| 1. Lactose | 0.236 | 7 | 1.652 | 0.0337 | $0.49 \times 10^5$ |
| 2. Galactose | 0.040 | 9 | 0.360 | 0.0035 | $1.00 \times 10^5$ |
| 3. Melibiose | 0.052 | 4 | 0.208 | 0.0042 | $0.44 \times 10^5$ |
| 4. N-Acetyl-D-galactosamine | 0.128 | 8 | 1.024 | 0.080 | $0.12 \times 10^5$ |
| 5. Fucose | 0.920 | 8 | 0.734 | 0.050 | $0.14 \times 10^5$ |
| Affinity columns eluted with buffer containing corresponding sugars (Non-$Ca^{++}$ dependent sugar-binding proteins) | | | | | |
| 1. Lactose | 0.158 | 11 | 1.738 | 0.0079 | $2.2 \times 10^5$ |
| 2. Galactose | 0.128 | 10 | 1.280 | 0.0156 | $0.8 \times 10^5$ |
| 3. Melibiose | 0.200 | 8 | 1.600 | 0.345 | $0.4 \times 10^5$ |
| 4. N-Acetyl-D-galactosamine | 0.140 | 10 | 1.140 | 0.0044 | $3.2 \times 10^5$ |
| 5. Fucose | 0.148 | 9 | 1.332 | 0.360 | $0.36 \times 10^5$ |

[a]Inhibitory concentration expressed as $\mu$g protein/ml which caused 50% inhibition of the growth of L1210 cells in culture.
[b]Activity unit is defined as dilution factor needed for a specific fraction which when added to L1210 cells caused a 50% cell growth inhibiton.

TABLE 4

FRACTIONATION OF BIOLOGICALLY ACTIVE CARBOHYDRATE BINDING PROTEINS FROM ISCADOR 'M', (20%)

| Fraction identity | Protein Content (mg/ml) | Total Volume (ml) | Total Protein (mg) | $ID^a_{50}$ ($\mu$g Protein/ml) | Total Activity Units[b] |
|---|---|---|---|---|---|
| Iscador 'M', 20% | 4.6 | 12 | 55 | 0.25 | $2.2 \times 10^5$ |
| Fractions from G-75 column (21–65) | 0.315 | 65 | 20.50 | 0.078 | $2.6 \times 10^5$ |
| Affinity columns eluted with EDTA buffer | | | | | |
| 1. Lactose | 0.203 | 10 | 2.08 | 0.39 | $0.57 \times 10^4$ |
| 2. Galactose | 0.064 | 12 | 0.70 | 0.07 | $0.63 \times 10^4$ |
| 3. Melibiose | 0.182 | 12 | 2.20 | 0.90 | $1.20 \times 10^4$ |

TABLE 4-continued

FRACTIONATION OF BIOLOGICALLY ACTIVE CARBOHYDRATE BINDING PROTEINS FROM ISCADOR 'M', (20%)

| Fraction identity | Protein Content (mg/ml) | Total Volume (ml) | Total Protein (mg) | $ID_{50}$[a] ($\mu$g Protein/ml) | Total Activity Units[b] |
|---|---|---|---|---|---|
| 4. N-Acetyl-D-galactosamine | 9.048 | 12 | 0.50 | 0.29 | $0.35 \times 10^4$ |
| 5. Fucose | 0.151 | 9 | 1.36 | 0.28 | $0.80 \times 10^4$ |
| Affinity columns eluted with buffer containing corresponding sugars | | | | | |
| 1. Lactose | 0.053 | 8.5 | 0.45 | 0.30 | $0.15 \times 10^4$ |
| 2. Galactose | 0.080 | 9 | 0.70 | 0.26 | $0.27 \times 10^4$ |
| 3. Melibiose | 0.009 | 7 | 0.06 | 0.035 | $0.17 \times 10^4$ |
| 4. N-Acetyl-D-galactosamine | 0.066 | 12.5 | 0.82 | 0.027 | $3.00 \times 10^4$ |
| 5. Fucose | 0.198 | 10.5 | 2.07 | 0.55 | $0.38 \times 10^4$ |
| Unbound proteins (after sugar buffer elution) | 0.225 | 50 | 11.Z5 | 0.25 | $4.5 \times 10^4$ |

[a]Inhibitory concentration expressed as $\mu$g protein/ml which caused 50% inhibition of the growth of L1210 cells in culture.
[b]Activity unit is defined as dilution factor needed for a specific fraction which when added to L1210 cells caused a 50% cell growth inhibition.

TABLE 5

EFFECT OF FERMENTATION ON THE BIOLOGICAL ACTIVITY OF CARBOHYDRATE BINDING PROTEINS (LECTINS) OF VISCUM ALBUM L. (ISCADOR 'M')

| Protein | T4GEN (A.U.) | ISCADOR (A.U.) | % Change (±) |
|---|---|---|---|
| ($Ca^{++}$ dependent sugar-binding proteins) | | | |
| 1. Lactose | $0.49 \times 10^5$ | $0.02 \times 10^5$ | −95.0 |
| 2..Galactose | $1.00 \times 10^5$ | $0.12 \times 10^5$ | −88.0 |
| 3. Melibiose | $0.44 \times 10^5$ | $0.07 \times 10^5$ | −84.1 |
| 4. N-Acetyl-D-galactosamine | $0.12 \times 10^5$ | $0.01 \times 10^5$ | −97.1 |
| 5. Fucose | $0.14 \times 10^5$ | $0.02 \times 10^5$ | −85.7 |
| (Non-$Ca^{++}$ dependent sugar-binding proteins) | | | |
| 1. Lactose | $2.20 \times 10^5$ | $0.20 \times 10^5$ | −91.0 |
| 2. Galactose | $0.80 \times 10^5$ | $0.02 \times 10^5$ | −97.5 |
| 3. Melibiose | $0.40 \times 10^5$ | $0.06 \times 10^5$ | −85.0 |
| 4. N-Acetyl-D-galactosamine | $3.20 \times 10^5$ | $0.72 \times 10^5$ | −77.5 |
| 5. Fucose | $0.36 \times 10^5$ | $0.01 \times 10^5$ | −97.3 |

*ISCADOR 'M', 20% and T4GEN (10%) were used as examples of fermented and unfermented mistletoe clinical preparations. Activity is described as total activity units as described elsewhere.

TABLE 6

GENERAL QUANTITATIVE FINGERPRINT PHARMACEUTICAL GRADE MISTLETOE EXTRACT

| | Percentage By Weight of Total Protein in Extract |
|---|---|
| ($Ca^{++}$ dependent sugar-binding proteins) | |
| 1. Lactose | 0.1–2.3 |
| 2. Galactose | 0.1–0.9 |
| 3. Melibiose | 0.1–0.6 |
| 4. N-Acetyl-D-galactosamine | 0.1–1.6 |
| 5. Fucose | 0.1–1.3 |
| (Non-$Ca^{++}$ dependent sugar-binding proteins) | |
| 1. Lactose | 0.1–2.4 |
| 2. Galactose | 0.1–1.9 |
| 3. Melibiose | 0.1–2.2 |
| 4. N-Acetyl-D-galactosamine | 0.1–2.8 |
| 5. Fucose | 0.1–2.0 |

TABLE 7

QUANTITATIVE FINGERPRINT FOR PHARMACEUTICAL GRADE EUROPEAN MISTLETOE EXTRACT

| | Percentage By Weight of Total Protein in Extract |
|---|---|
| ($Ca^{++}$ dependent sugar-binding proteins) | |
| 1. Lactose | 1.3–2.3 |
| 2. Galactose | 0.1–0.9 |
| 3. Melibiose | 0.1–0.6 |
| 4. N-Acetyl-D-galactosamine | 0.5–1.6 |
| 5. Fucose | 0.3–1.3 |
| (Non-$Ca^{++}$ dependent sugar-binding proteins) | |
| 1. Lactose | 1.4–2.4 |
| 2. Galactose | 0.9–1.9 |
| 3. Melibiose | 1.2–2.2 |
| 4. N-Acetyl-D-galactosamine | 0.8–2.8 |
| 5. Fucose | 1.0–2.0 |

TABLE 8

QUANTITATIVE FINGERPRINT FOR PHARMACEUTICAL GRADE KOREAN MISTLETOE EXTRACT

| | Percentage By Weight of Total Protein in Extract |
|---|---|
| ($Ca^{++}$ dependent sugar-binding proteins) | |
| 1. Lactose | 0.1–0.5 |
| 2. Galactose | 0.1–0.5 |
| 3. Melibiose | 0.1–0.5 |
| 4. N-Acetyl-D-galactosamine | 0.1–0.5 |
| 5. Fucose | 0.1–0.5 |
| (Non-$Ca^{++}$ dependent sugar-binding proteins) | |
| 1. Lactose | 0.1–0.5 |
| 2. Galactose | 0.1–0.8 |
| 3. Melibiose | 0.1–0.5 |
| 4. N-Acetyl-D-galactosamine | 0.1–0.7 |
| 5. Fucose | 0.1–0.5 |

TABLE 9

QUANTITATIVE AND BIOACTIVITY FINGERPRINTS FOR PHARMACEUTICAL GRADE MISTLETOE EXTRACT

| | Concentration (mg/ml) | Inhibitory Concentration (ID$_{50}$) |
|---|---|---|
| ($Ca^{++}$ dependent sugar-binding proteins) | | |
| 1. Lactose | 0.1–0.5 | 0.01–0.5 |
| 2. Galactose | 0.01–0.5 | 0.001–0.5 |
| 3. Melibiose | 0.01–0.5 | 0.001–0.5 |
| 4. N-Acetyl-D-galactosamine | 0.1–1.0 | 0.01–0.5 |
| 5. Fucose | 0.1–1.0 | 0.01–0.5 |
| (Non-$Ca^{++}$ dependent sugar-binding proteins) | | |
| 1. Lactose | 0.1–0.5 | 0.0001–0.1 |
| 2. Galactose | 0.1–2.0 | 0.001–0.1 |
| 3. Melibiose | 0.1–0.5 | 0.001–0.5 |
| 4. N-Acetyl-D-galactosamine | 0.1–1.0 | 0.001–0.1 |
| 5. Fucose | 0.1–1.5 | 0.01–0.5 |

TABLE 10

QUANTITATIVE AND BIOACTIVITY FINGERPRINTS FOR PHARMACEUTICAL GRADE EUROPEAN MISTLETOE EXTRACT

| | Concentration (mg/ml) | Inhibitory Activity (ID$_{50}$) |
|---|---|---|
| ($Ca^{++}$ dependent sugar-binding proteins) | | |
| 1. Lactose | 0.1–0.3 | 0.01–0.1 |
| 2. Galactose | 0.01–0.1 | 0.0001–0.01 |
| 3. Melibiose | 0.01–0.1 | 0.001–0.01 |
| 4. N-Acetyl-D-galactosamine | 0.1–0.3 | 0.01–0.1 |
| 5. Fucose | 0.5–1.0 | 0.01–0.1 |
| (Non-$Ca^{++}$ dependent sugar-binding proteins) | | |
| 1. Lactose | 0.1–0.3 | 0.001–0.1 |
| 2. Galactose | 0.1–0.3 | 0.01–0.1 |
| 3. Melibiose | 0.1–0.3 | 0.1–0.5 |
| 4. N-Acetyl-D-galactosamine | 0.05–0.3 | 0.001–0.01 |
| 5. Fucose | 0.05–0.3 | 0.1–0.5 |

TABLE 11

QUANTITATIVE AND BIOACTIVITY FINGERPRINTS FOR PHARMACEUTICAL GRADE KOREAN MISTLETOE EXTRACT

| | Concentration (mg/ml) | Inhibitory Activity (ID$_{50}$) |
|---|---|---|
| ($Ca^{++}$ dependent sugar-binding proteins) | | |
| 1. Lactose | 0.1–0.5 | 0.1–0.5 |
| 2. Galactose | 0.2–0.6 | 0.1–0.5 |
| 3. Melibiose | 0.1–0.5 | 0.1–0.5 |
| 4. N-Acetyl-D-galactosamine | 0.5–1.0 | 0.1–0.5 |
| 5. Fucose | 0.1–0.5 | 0.1–0.5 |
| (Non-$Ca^{++}$ dependent sugar-binding proteins) | | |
| 1. Lactose | 0.1–0.5 | 0.0001–0.009 |
| 2. Galactose | 1.0–2.0 | 0.001–0.01 |
| 3. Melibiose | 0.1–0.5 | 0.001–0.01 |
| 4. N-Acetyl-D-galactosamine | 0.5–1.0 | 0.001–0.1 |
| 5. Fucose | 1.0–2.0 | 0.001–0.1 |

TABLE 12

BIOLOGICAL ACTIVITY OF MISTLETOE EXTRACTS IN TERMS OF ACTIVITY UNITS (A.U.)

| Sample Identity | Activity units/ml, (1 % Extract) |
|---|---|
| 1. ISCADOR M, Arg., 10% | 80 |
| 2. n-T4GEN, 40% | 400 |
| 3. T4GEN, 5% | 227 |
| 4. ISCADOR M, 5% | 30 |
| 5. ISCADOR M, 20% | 37 |
| 6. T4GEN, 1% | 140 |
| 7. T4GEN, 10% | 217 |
| 8. ISCADOR M, 20% | 26 |
| 9. n-T4GEN, 40% | 416 |
| 10. n-T4GEN | 192 |
| 11. n-T4GEN | 811 |

$$\text{Activity unit per ml} = \frac{\text{concentration of sample in } \mu g/ml}{ID_{50}(\mu g/ml)}.$$

EXAMPLE 4

Preparation of Pharmaceutical Grade Water Extract

An extract from Korean mistletoe was prepared by taking a known weight of plant (100 g) and cleaning and crushing it in the presence of double distilled water to form a 40% by weight solution of mistletoe. It is preferred that the plant be cut and the cuttings put in a plastic bag and flash frozen in liquid nitrogen prior to being crushed and combined with the distilled water. The crushing and combination of the frozen material with the distilled water is preferably carried out in a blender for about 2 minutes. The resulting mixture is centrifuged at 10,000 rpm for 65 minutes to separate extract from insoluble residue. The residue is twice extracted with known volumes (100 ml) of water to remove all extract and subjected to centrifugation. The supernatants are combined. The resulting extract is stored in the absence of air at room temperature for two weeks. The extract is then sterilized by step filtration as is conventionally known.

The sterile extract is then subjected to a preliminary screening test as previously described to determine if its bioactivity with respect to the L1210 leukemia system is 100 A.U. or more. If the extract passes this test, then it is subjected to the more rigorous tests as described in the prior Examples to determine its sugar-binding protein fingerprint. If the protein levels fall within the limits required in accordance with the present invention, then the extract is identified as pharmaceutical grade. Table 13 sets forth the results of testing of an extract prepared as above. As can be seen, the extract has concentration levels and bioactivity values which fall within the standard fingerprint limits which are required for it to be identified as pharmaceutical grade in accordance with the present invention.

TABLE 13

FRACTIONATION OF DIFFERENT BIOLOGICALLY ACTIVE CARBOHYDRATE BINDING PROTEINS FROM VISCUM ALBUM C. EXTRACT (40%, FrF) (n-T4GEN)

| Fraction identity | Total Volume (ml) | Total Protein (mg) | $ID_{50}$ | $ID_{50}^a$ (μg/ml) | Total Activity Units[b] |
|---|---|---|---|---|---|
| Extract (40%, FrF) | 90 | 234 | 32,500 | | $2.92 \times 10^6$ |
| Affinity columns eluted with EDTA buffer | | | | | |
| 1. Lactose | 5.5 | 4.29 | 175 | 1.10 | $0.10 \times 10^4$ |
| 2. Galactose | 11.5 | 2.10 | 415 | 0.49 | $0.50 \times 10^4$ |
| 3. Melibiose | 10 | 1.36 | 315 | 0.40 | $0.30 \times 10^4$ |
| 4. N-Acetyl-D-galactosamine | 7 | 0.95 | 400 | 0.33 | $0.28 \times 10^4$ |
| 5. Fucose | 5 | 1.82 | 365 | 1.00 | $0.18 \times 10^4$ |
| Affinity columns eluted with buffer containing corresponding sugars | | | | | |
| 1. Lactose | 8 | 2.24 | 208,000 | 0.001 | $1.66 \times 10^6$ |
| 2. Galactose | 11 | 2.68 | 68,000 | 0.0035 | $0.75 \times 10^6$ |
| 3. Melibiose | 6.5 | 0.96 | 5,600 | 0.025 | $0.036 \times 10^6$ |
| 4. N-Acetyl-D-galactosamine | 4.5 | 0.81 | 49,000 | 0.0035 | $0.22 \times 10^6$ |
| 5. Fucose | 5 | 0.33 | 10,500 | 0.0056 | $0.052 \times 10^6$ |
| Unbound proteins and alkaloids | 168 | 285 | 1,600 | 1.25 | $0.27 \times 10^6$ |

[a]Dilution factor needed per ml to cause 50% inhibition of L1210 cells in culture.
[b]Activity unit is defined as dilution factor needed for a specific fraction which when added to L1210 cell will cause 50% inhibition of the cell growth.

EXAMPLE 5

Preparation of Total Extract of Korean Mistletoe

An extract of Korean mistletoe was prepared by taking 100 g of mistletoe, freezing it and powdering it. The frozen powder was then thawed and extracted with 200 ml of cold acetone. The extraction mixture was centrifuged at 10,000 rpm for 60 minutes. The precipitate was washed with two 100 ml aliquots of cold acetone and centrifuged again at 10,000 rpm for 60 minutes. The resulting extract residue is extracted with two 200 ml aliquots of Buffer A (see Example 2) in a blender for 2 minutes each. The two extract aliquots are centrifuged at 10,000 rpm for 60 minutes and the supernatants combined. The extract residue is extracted a final time with an additional 200 ml of Buffer A. After centrifugation, this final extractant is combined with the other two aliquots to form a salt extract which after removal of salts, is then tested in accordance with the present invention to determine if its sugar-binding protein fingerprint meets the pharmaceutical grade requirements set forth above.

The extract residue remaining after the above extraction with Buffer A may be extracted with a detergent extract— Buffer B (see Example 2)— to form an extract which, after dialysis to remove detergents and salts, also can be tested to determine if it meets the pharmaceutical grade requirements of the present invention.

EXAMPLE 6

Isolation of Biologically Active Components of Coriolus Versicolor 650 mg of Crude coriolus versicolor powder polysaccharide peptide (PSP) (Landford, 18 capsules lot #941231) were added to 45 ml of a buffer C (see Example 2) and stirred at 4° C. overnight. Next day the solution was centrifuged (10,000 r.p.m., 1 hour), and the supernatant was removed and passed through a series of sugar specific columns (flow rate 6 ml per hour). The columns were washed with buffer C to remove all unbound proteins. Then each column was washed with a buffer D (see Example 2) containing EDTA (10 column volume). These eluates were separately collected and each contained carbohydrate binding proteins which require $Ca^{++}$ for their binding specificities.

Then each column was washed with buffer C and then separately eluted with buffer C containing 0.5 M sugars (lactose, galactose and melibiose). Each eluate was collected and each contained carbohydrate binding proteins which do not require $Ca^{++}$ for their binding specificities.

All six eluates were concentrated using 5K cutoff ultramembrane filters to remove salts and low molecular weight components.

The biological activities of each protein and the materials which did not bind to the columns were assayed in the same leukemia L1210 system in culture as was used in the preceding examples. The protein contents of each sample were assayed by Bio Rad and molecular weight of samples were assayed by 6.5% SDS gels.

The total proteins isolated 13.87 mg yield=13.87×100/6.05=2.29%

The quantitative and bioactivity protein fingerprints for the sample of Coriolus Versicolor are set forth in Table 14. The standard fingerprints which were established for pharmaceutical grade are set forth in Table 15. A comparison of the fingerprints for the sample and standard shows that they match so the sample qualifies as pharmaceutical grade in accordance with the present invention.

TABLE 14

QUANTITATIVE AND BIOACTIVITY FINGERPRINT OF CORIOLUS VERSICOLOR SAMPLE

| Fraction Identity | Protein Content (mg/ml) | Total Volume (ml) | Total Protein (mg) | $ID_{50}^a$ (ug/ml) | Total[a] Activity Units |
|---|---|---|---|---|---|
| PSP | 13.4 | 45 | 603 | — | — |
| EDTA Eluted Proteins | | | | | |
| Lactose | 0.430 | 5.0 | 2.15 | 0.0600 | $3.5 \times 10^4$ |
| Galactose | 0.240 | 6.0 | 1.44 | 0.0210 | $6.8 \times 10^4$ |
| Melibiose | 0.480 | 6.5 | 3.12 | 0.0033 | $91.0 \times 10^4$ |
| 0.5 M Sugar Eluted Proteins | | | | | |
| Lactose | 0.370 | 8.5 | 3.14 | 0.028 | $11.0 \times 10^4$ |
| Galactose | 0.459 | 7.5 | 3.44 | 0.110 | $3.1 \times 10^4$ |
| Melibiose | 0.074 | 6.0 | 0.44 | 0.150 | $0.2 \times 10^4$ |
| Unbound Sugars | 3.950 | 136.0 | 537 | — | — |

[a]Inhibitory concentrations (μg/ml) which caused 50% inhibition of the growth of L1210 leukemia cells in culture
[b]Activity unit is defined as the dilution factor needed for a specific fraction which added to L1210 cells in culture causes 50% growth inhibition.

TABLE 15

STANDARD QUANTITATIVE AND BIOACTIVITY FINGERPRINT OF CORIOLUS VERSICOLOR

| Fraction Identity | Protein Content (mg/ml) | $ID_{50}$[a] (ug/ml) | Total[a] Activity Units |
|---|---|---|---|
| PSP | — | — | — |
| EDTA Eluted Proteins | | | |
| Lactose | 0.2–0.6 | 0.01–0.10 | $1.0–10.0 \times 10^4$ |
| Galactose | 0.1–0.4 | 0.01–0.10 | $5.0–15.0 \times 10^4$ |
| Melibiose | 0.3–0.6 | 0.001–0.01 | $50–150 \times 10^4$ |
| 0.5 M Sugar Eluted Proteins | | | |
| Lactose | 0.1–0.5 | 0.01–0.10 | $5.0–20 \times 10^4$ |
| Galactose | 0.3–0.6 | 0.1–0.5 | $1.0–10 \times 10^4$ |
| Melibiose | 0.01–0.10 | 0.1–0.5 | $0.1–5.0 \times 10^4$ |

[a]Inhibitory concentrations (μg/ml) which caused 50% inhibition of the growth of L1210 leukemia cells in culture.
[b]Activity unit is defined as the dilution factor needed for a specific fraction which added to L1210 cells in culture causes 50% growth inhibition.

Figure 4:
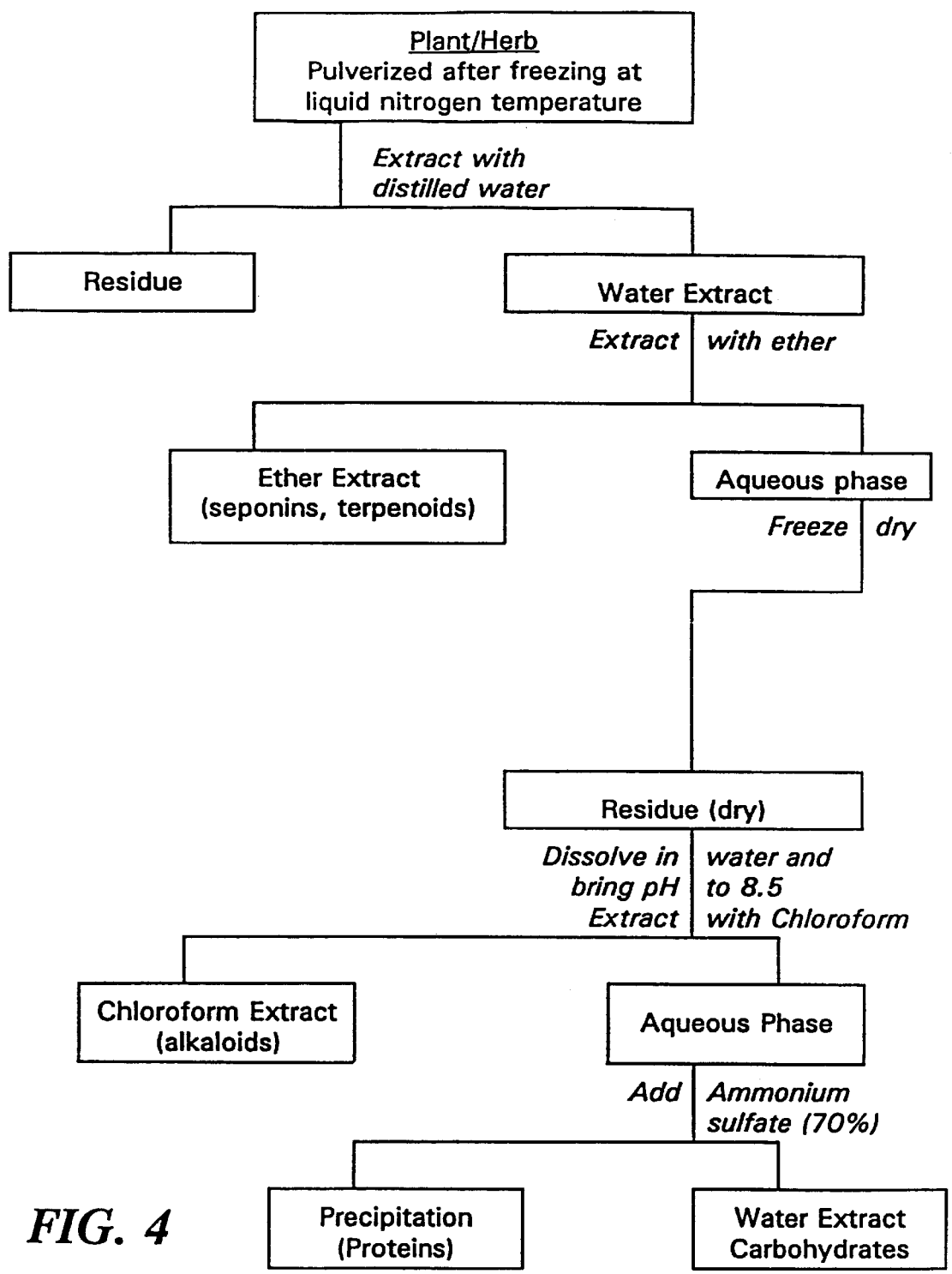
FIG. 4 is a schematic representation of a procedure for isolating different classes of biologically active components.

An exemplary general method for separating plants into major classes of chemical components is set forth schematically in FIG. 4. Primarily fresh plants (including leaves, roots, flowers, berries and stem) should be used. Specific plant parts, such as the leaves, flowers, stems or root may be used if desired.

The specific part or whole plant is frozen at liquid nitrogen temperature. This facilitates grinding and also preserves the integrity and potency of the active ingredients.

The pulverized powder is extracted with distilled water (repeatedly). If desired, the extraction may be carried out with hot water, alcohol, aqueous alcohol or dilute acetic acid. The actual temperature chosen is preferably close to or at the boiling temperature of water. It is preferred that the overall bioactivity of the aqueous extract be initially determined. The combined water extracts are subjected to a specific bioassay (e.g. a test for inhibiting the growth of bacteria in Petri dishes if the drug is to be used as antibacterial. Alternatively, tests against cell cultures of cancer cells are conducted preferably if the drug is intended for use as an anticancer agent. From these data bioactivity units contained in an extract per ml are calculated (bioactivity units are defined in number of dilution of this extract needed to inhibit 50% growth of bacterium or cancer cell in test system.

For establishing fingerprints in accordance with the present invention, the plant is extracted according to the procedure as set forth in FIG. 4 to separate it into major components (e.g. saponins, terpenoids, lipids, alkaloids, nucleic acids, proteins and carbohydrate). Each separated group of components is tested for bioactivity as needed. This may point to activity (e.g. in protein and alkaloid factions as in viscum album). The active class or classes of compounds are further separated into individual components by affinity chromatography or high pressure liquid chromatography or gas chromatography. The components with major contribution towards biological activity are quantified on the basis of weight and specific bioactivity units. These components provide the fingerprint to establish the pharmaceutical requirements for the original herbal extract. The bioactivity units per ml of the pharmaceutical grade extract provide a way to establish exact doses for clinical studies.

Further examples of practice are as follows:

EXAMPLE 7

Fingerprinting Saw Palmetto Berry (Serenoa repens) Extract

Extract of saw palmetto berry have been used as a herbal remedy for the treatment of benign prostate enlargement or benign prostatic hypertrophy (BPH). BPH is generally associated with age and occurs principally in males over 50. It is believed to be caused by conversion of testosterone present in prostate to dihydrotestosterone by an enzyme testosterone-5-alpha reductase. The conversion may be due to increased levels of this enzyme in the prostatic tissue. Increased levels of dihydrotestosterone are believed to cause overproduction of prostate cells and prostate enlargement. In such cases serum levels of prostatic specific antigen (PSA) may also increase. A drug (PROSCAR®) has been used which inhibits the enzyme 5-alpha reductase and thus inhibits high concentrations of dihydrotestosterone in prostate and consequently prostate enlargement. Clinical studies describe limited success with PROSCAR® therapy which also results in side effects. A report in *American Journal of Natural Medicine* (September 1994) presents a comparison of the therapeutic effects of saw palmetto berry extracts with PROSCAR®. However, due to the unknown nature of the extract composition, these studies cannot be examined in controlled clinical trials. There are reports that fat soluble extracts of saw palmetto berries are better able to relieve the major symptoms of BPH.

To prepare a pharmaceutical grade drug in accordance with the present invention, the aqueous extract of the berries is separated into its components as set forth in FIG. 4. Each specific component including the original extract is tested as an inhibitor of testosterone-5-alpha reductase (possibly by its ability to inhibit the incorporation of tritium into testosterone as compared to untreated controls). Those tests will point to lipid soluble components which include lipids, saponins and alkaloids. The components with the most activity in this bioassay are further separated into individual molecules by gas chromatography or high pressure liquid chromatography. Thus, in preparative mode, each component is separated and evaluated in the reductase system for its specific bioactivity. The components which contribute to highest bioactivity are used to prepare the quantitative and bioactivity fingerprints for saw palmetto berry aqueous extracts. The specific bioactivity units of the extract can be used to provide exact dose of the natural pharmaceutical for its clinical trial as a drug for the treatment of benign prostatic hypertrophy. Once the fingerprints have been established, they are used to verify that later processed berry extracts meet the standards of pharmaceutical grade materials as outlined in the procedure set forth in FIG. 2.

EXAMPLE 8

Fingerprinting Echinacea Extract (Echinacea angustifolia)

*Echinacea angustifolia*, often called purple cornflower, is a plant of North American origin. Native Americans have used extracts from this plant for wound healing (antibiotic) and as an anti-inflammatory agent. Freshly squeezed juices of leaves and roots from this plant have been approved by the German government for the treatment of recurrent infections of respiratory and urinary tracts. Liquid echinacea preparations have been shown to have immune stimulatory activity when administered orally or parenterally. It is believed that the activation of splenocytes may contribute to the extract's ability to enhance the activity of granulocytes and phagocytes. Echinacea extract has also been used as an anti-AIDS agent.

For fingerprinting in accordance with the present invention, green leaves and roots are cut and frozen at less than −100° C. The mixture is then pulverized and extracted with known volume of water. This procedure is preferred to retain the maximum amounts of active ingredients. The active ingredients are a mix of volatile oils, glycosides, amides and polyacetylenes.

The extract is separated into basic classes of components following the procedure set forth in FIG. 4. Each separated class of components is subjected to two types of bioassays (as well as the original extract). The first assay measures the antibacterial activity in cultures of E. coli using the turbidity of growing E. coli as a measure of their growth. Lack of turbidity in the presence of a given test extract or its components provides an indication of antibacterial activity. The second assay measures activation of spleen cells in C57BL/6 mice. The mice are sensitized with P815Y lymphoma and treated with different doses of the sterile extract or specific components. After 11 days post lymphoma cell inoculation, the spleens are harvested and splenocytes used to challenge P815Y lymphoma cells loaded with $^{51}$Cr. The release of the radioactive $^{51}$Cr from tumor cells provides a measure (radioactive counts) of the activation of splenocytes (the assay system).

The most bioactivity associated components (e.g. terpenoids) are separated by GC, GC/Ms or HPLC technology into individual components which are used to provide fingerprints in accordance with the present invention.

The scientific articles and other references referred to in this specification are hereby specifically all incorporated by reference.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for standardizing a botanical material as part of a manufacturing procedure yielding pharmaceutical grade botanical material, said botanical material having one or more measurable biological activities as measurable in one or more bioassays, and said botanical material comprising a plurality of bioactive components, the method comprising:
   (a) removing at least one representative aliquot from said botanical material, and determining therefrom the total amount of at least one measurable biological activity exhibited by said botanical material as measured according to at least one bioassay, to provide at least one total bioactivity amount of the unfractionated homogeneous botanical material;
   (b) comparing the total bioactivity amount determined in step (a) to a total bioactivity standard for pharmaceutical grade botanical material, to provide a total bioactivity comparison;
   (c) removing at least one second representative aliquot from said botanical material, fractionating the second aliquot into a plurality of fractions each containing different components of said second representative aliquot, and determining in said fractions the amount of each of one or more bioactive components previously specified in a fingerprint standard for pharmaceutical grade botanical material, to provide a fingerprint for said botanical material;
   (d) comparing said fingerprint to said fingerprint standard previously defined for pharmaceutical grade botanical material, to provide a fingerprint comparison;
   (e) determining whether said botanical material is said pharmaceutical grade botanical material based on (1) said total bioactivity comparison and (2) said fingerprint comparison.

2. The method of claim 1 wherein said fingerprint standard was previously established according to a method comprising the steps of:
   (a) providing botanical material having said one or more measurable biological activities as measurable in one or more bioassays, which botanical material comprises many components including one or more bioactive components each having a biological activity as measurable in one or more bioassays;
   (b) measuring said one or more biological activities in said botanical material using at least two bioassays;
   (c) measuring the biological activity of the many components of said botanical material to identify all of said one or more bioactive components having biological activity in either or both of said at least two bioassays;
   (d) identifying those said bioactive components that account for a majority of at least one of said biological activities in said botanical material; and
   (e) establishing said fingerprint so as to include said identified bioactive components that account for a majority of at least one of said biological activities in said botanical material.

3. The method of any of claim 1 or 2 wherein said fingerprint standard specifies a concentration range of said one or more components.

4. The method of any of claim 1 or 2 wherein said fingerprint standard specifies a range of bioactivity of said one or more components.

5. The method of any of claim 1 or 2 wherein at least one of the components specified in said fingerprint standard is an individual molecule component.

6. The method of any of claim 1 or 2 wherein at least one of the components specified in said fingerprint standard comprises a group of two or more distinct individual molecule components.

7. The method of any of claim 1 or 2 wherein said unfractionated homogeneous botanical material is a powder made from one or more plants or plant parts.

8. The method of any of claim 1 or 2 wherein said unfractionated homogeneous botanical material is an extract derived from one or more plants or plant parts.

9. The method of claim 2 wherein and the bioassay used to provide the total bioactivity amount of the unfractionated homogeneous botanical material is one of said at least two bioassays.

10. The method of claim 2 wherein the bioassay used to provide the total bioactivity amount of the unfractionated homogeneous botanical material is a bioassay different from each of said at least two bioassays.

11. The method of any of claim 1 or 2 wherein said botanical material is selected from the group consisting of mistletoe, coriolus versicolor, saw palmetto, echinacea, garlic, St. John's Wort and fenugreek.

12. The method of any of claim 1 or 2 wherein said fingerprint includes components which are effective in the treatment of AIDS.

13. The method of any of claim 1 or 2 wherein said fingerprint includes components which are effective in the treatment of cancer.

14. The method of claim 1 wherein said at least one measurable biological activity is an inhibition of cancerous growth.

15. The method of claim 1 wherein at least one of said one or more bioassays measures anti-cancer activity.

16. The method of claim 2 wherein at least one of said one or more bioassays measures anti-HIV activity.

17. A method for determining whether a botanical material is a pharmaceutical grade botanical material, said method comprising the steps of:
   providing a homogenous processed botanical material having a given biological activity which material comprises a plurality of components wherein one or more of the components are active components and the active components are responsible for the majority of the biological activity;
   removing an aliquot from said botanical material;
   separating said aliquot into a plurality of marker fractions wherein each of said marker fractions comprises one of said active components;
   determining the amount of said given biological activity for each of said marker fractions to provide a bioactivity fingerprint of said aliquot;
   comparing the bioactivity fingerprint of said aliquot to a bioactivity fingerprint standard which specifies the bioactivity of components with the majority of the bioactivity, which standard has been previously established for a pharmaceutical grade botanical material, to provide a bioactivity fingerprint comparison;
   determining the amount of said given biological activity of a second aliquot from said botanical material in a bioassay to provide a total bioactivity of the botanical material;
   comparing the total bioactivity of the botanical material to a total bioactivity standard which has been previously established to provide a total bioactivity comparison; and
   determining whether said processed botanical material is pharmaceutical grade botanical material based on said bioactivity fingerprint comparison and said total bioactivity comparison.

18. A method according to claim 17 wherein said method comprises the additional steps of:
   determining the amount of said components in each of said marker fractions to provide a quantitative fingerprint of said aliquot;
   comparing the quantitative fingerprint of said aliquot to a quantitative fingerprint standard which has been previously established for a given pharmaceutical grade botanical material to thereby provide a quantitative fingerprint comparison; and
   determining whether said processed botanical material is a pharmaceutical grade botanical material based on said quantitative fingerprint comparison as well as said bioactivity fingerprint comparison and said total bioactivity comparison.

19. The method of claim 17 wherein said biological activity is an anti-cancer activity.

20. The method of claim 17 wherein said biological activity is an anti-HIV activity.

21. The method of any of claim 17, 18, 19 or 20 or wherein said method is performed as part of a manufacturing procedure yielding said pharmaceutical grade botanical material.

22. The method of any of claim 1 or 2, wherein said method is employed to reiteratively test a batch of said botanical material to insure that only pharmaceutical grade botanical material is approved.

23. The method of any of claim 17 or 18 wherein said method is employed to reiteratively test a batch of said botanical material to insure that only pharmaceutical grade botanical material is approved.

24. A method for determining whether a botanical material is a pharmaceutical grade botanical material suitable for the treatment of AIDS, said method comprising the steps of:
   providing a homogenous processed botanical material having an anti-HIV biological activity which material comprises a plurality of components wherein one or more of the components are active components and the active components are responsible for the majority of the anti-HIV biological activity;
   removing an aliquot from said botanical material;
   separating said aliquot into a plurality of marker fractions wherein each of said marker fractions comprises one of said active components;
   determining the amount of said anti-HIV biological activity for each of said marker fractions to provide a bioactivity fingerprint of said aliquot;
   comparing the bioactivity fingerprint of said aliquot to a bioactivity fingerprint standard which specifies the bioactivity of components with the majority of the bioactivity, which standard has been previously established for a pharmaceutical grade botanical material, to provide a bioactivity fingerprint comparison;
   determining the amount of said anti-HIV biological activity of a second aliquot from said botanical material in a bioassay to provide a total bioactivity of the botanical material;
   comparing the total bioactivity of the botanical material to a total bioactivity standard which has been previously established to provide a total bioactivity comparison; and determining whether said processed botanical material is pharmaceutical grade botanical material based on said bioactivity fingerprint comparison and said total bioactivity comparison.

25. The method of claim 24 wherein said botanical material is mistletoe.

26. A method for determining whether a botanical material is a pharmaceutical grade botanical material suitable for the treatment of cancer, said method comprising the steps of:
   providing a homogenous processed botanical material having an anti-cancer biological activity which material comprises a plurality of components wherein one or more of the components are active components and the active components are responsible for the majority of the anti-cancer biological activity;
   removing an aliquot from said botanical material;
   separating said aliquot into a plurality of marker fractions wherein each of said marker fractions comprises one of said active components;
   determining the amount of said anti-cancer biological activity for each of said marker fractions to provide a bioactivity fingerprint of said aliquot;
   comparing the, bioactivity fingerprint of said aliquot to a bioactivity fingerprint standard which specifies the bioactivity of components with the majority of the bioactivity, which standard has been previously established for a pharmaceutical grade botanical material to provide a bioactivity fingerprint comparison;

determining the amount of said anti-cancer biological activity of a second aliquot from said botanical material in a bioassay to provide a total bioactivity of the botanical material;

comparing the total bioactivity of the botanical material to a total bioactivity standard which has been previously established to provide a total bioactivity comparison; and determining whether said processed botanical material is pharmaceutical grade botanical material based on said bioactivity fingerprint comparison and said total bioactivity comparison.

27. The method of claim 26 wherein said botanical material is mistletoe.

28. The method of claim 26 wherein said anti-cancer biological activity is measured as an inhibitory action with respect to leukemia cells.

29. The method of claim 26 wherein said anti-cancer biological activity is measured as an inhibition of the growth of mammary adenocarcinoma.

30. A method for standardizing a botanical material and maintaining synergistic biological activity provided by said botanical material as part of a manufacturing process yielding pharmaceutical grade botanical material, said method comprising the steps of:

providing a homogenous processed botanical material having a given biological activity which material comprises a plurality of components wherein one or more of the components are active components and the active components are responsible for the majority of the biological activity;

removing an aliquot from said botanical material;

separating said aliquot into a plurality of marker fractions wherein each of said marker fractions comprises one of said active components;

determining the amount of said given biological activity for each of said marker fractions to provide a bioactivity fingerprint of said aliquot;

comparing the bioactivity fingerprint of said aliquot to a bioactivity fingerprint standard which specifies the bioactivity of components with the majority of the bioactivity, which standard has been previously established for a pharmaceutical grade botanical material, to provide a bioactivity fingerprint comparison;

determining the amount of said active components in each of said marker fractions to provide a quantitative fingerprint of said aliquot;

comparing the quantitative fingerprint of said aliquot to a quantitative fingerprint standard which has been previously established for a given pharmaceutical grade botanical material to thereby provide a quantitative fingerprint comparison;

determining the amount of said given biological activity of a second aliquot from said botanical material in a bioassay to provide a total bioactivity of the botanical material;

comparing the total bioactivity of the botanical material to a total bioactivity standard which has been previously established and quantitatively reflects synergistic biological activity to provide a total bioactivity comparison; and determining whether said processed botanical material is pharmaceutical grade botanical material based on said bioactivity fingerprint comparison, said quantitative fingerprint comparison and said total bioactivity comparison.

31. The method of claim 30 wherein said homogeneous processed botanical material is an extract derived from one or more plants or plant parts.

* * * * *